US012214161B2

(12) United States Patent
Jones et al.

(10) Patent No.: US 12,214,161 B2
(45) Date of Patent: Feb. 4, 2025

(54) POOLING DEVICE FOR SINGLE OR MULTIPLE MEDICAL CONTAINERS

(71) Applicant: Takeda Pharmaceutical Company Limited, Osaka (JP)

(72) Inventors: Seth Dale Jones, Round Lake, IL (US); Madeleine Clare Gibson, Madison, WI (US); Daniel Edward Roush, Niles, IL (US); Dhairya Kiritkumar Mehta, Waltham, MA (US); Sujit K. Basu, Newton, MA (US); Jennifer Craig Cordova, Highland Park, IL (US)

(73) Assignee: Takeda Pharmaceutical Company Limited, Osaka (JP)

( * ) Notice: Subject to any disclaimer, the term of this patent is extended or adjusted under 35 U.S.C. 154(b) by 980 days.

(21) Appl. No.: 17/282,042

(22) PCT Filed: Sep. 24, 2019

(86) PCT No.: PCT/US2019/052572
§ 371 (c)(1),
(2) Date: Apr. 1, 2021

(87) PCT Pub. No.: WO2020/072230
PCT Pub. Date: Apr. 9, 2020

(65) Prior Publication Data
US 2021/0369958 A1    Dec. 2, 2021

(51) Int. Cl.
*A61M 5/162*    (2006.01)
*A61M 5/14*    (2006.01)
*A61M 5/168*    (2006.01)

(52) U.S. Cl.
CPC ........ *A61M 5/1626* (2013.01); *A61M 5/1407* (2013.01); *A61M 5/16813* (2013.01);
(Continued)

(58) Field of Classification Search
CPC ............. A61M 5/1626; A61M 5/1407; A61M 5/16813; A61M 5/16822;
(Continued)

(56) References Cited

U.S. PATENT DOCUMENTS 363,690 A    5/1887    Sleeper
2,080,947 A    5/1937    Ligeour
(Continued)

FOREIGN PATENT DOCUMENTS

CN    1668352 A    9/2005
CN    1874936 A    12/2006
(Continued)

OTHER PUBLICATIONS

Invitation to Pay Additional Fees mailed Feb. 26, 2020 in connection with International Application No. PCT/US2019/052572.
(Continued)

*Primary Examiner* — Theodore J Stigell
(74) *Attorney, Agent, or Firm* — Wolf, Greenfield & Sacks, P.C.

(57) ABSTRACT

A medicinal fluid pooling device may be used to pool multiple containers of medicinal fluid to facilitate administration of the medicinal fluid to a patient. A medicinal pooling device may include spikes covered by spike sheaths which are pierced when a container of medicinal fluid is inserted into the medicinal pooling device. The medicinal pooling device may also include a cover configured to cover the spikes. The medicinal pooling device may also include a fluidic interface which may be used to fluidly connect the medicinal pooling device to an infusion pump or syringe.

13 Claims, 25 Drawing Sheets

(52) U.S. Cl.
CPC ... *A61M 5/16822* (2013.01); *A61M 2209/045* (2013.01); *A61M 2209/088* (2013.01)

(58) Field of Classification Search
CPC ...... A61M 2209/045; A61M 2209/088; A61M 5/162; A61M 5/16827; A61M 39/26; A61M 5/14244; A61J 1/20; A61J 3/002; A61J 1/2089
See application file for complete search history.

(56) References Cited

U.S. PATENT DOCUMENTS

| | | |
|---|---|---|
| 2,399,893 A | 5/1946 | Scholz |
| D159,762 S | 8/1950 | Touhey |
| 2,754,962 A | 7/1956 | Scrymgeour |
| 2,865,669 A | 12/1958 | Linthicum |
| 2,949,204 A | 8/1960 | Edwards |
| 3,278,007 A | 10/1966 | Weber |
| 3,543,355 A | 12/1970 | Wyckoff et al. |
| 3,589,509 A | 6/1971 | Mascia et al. |
| 3,593,873 A | 7/1971 | Vonk |
| 3,601,253 A | 8/1971 | Poupitch |
| 3,727,749 A | 4/1973 | Martin |
| 3,744,661 A | 7/1973 | Fischer, Jr. |
| 3,876,377 A | 4/1975 | Cinqualbre |
| 3,882,909 A | 5/1975 | Ogle |
| 3,893,280 A | 7/1975 | King |
| 4,143,764 A | 3/1979 | Moss, III |
| 4,178,152 A | 12/1979 | Nunogaki |
| 4,262,814 A | 4/1981 | Roccaforte |
| 4,402,691 A | 9/1983 | Rosenthal et al. |
| 4,405,315 A | 9/1983 | Handt |
| 4,526,756 A | 7/1985 | Wong |
| D280,932 S | 10/1985 | Green |
| 4,557,727 A | 12/1985 | Handt |
| D283,640 S | 4/1986 | Grimes |
| 4,713,064 A | 12/1987 | Bruno et al. |
| 4,759,756 A | 7/1988 | Forman et al. |
| 4,795,429 A | 1/1989 | Feldstein |
| 4,807,777 A | 2/1989 | Berwald et al. |
| 4,850,972 A | 7/1989 | Schulman et al. |
| 4,856,647 A | 8/1989 | Dahne |
| 4,863,049 A | 9/1989 | Suzuki et al. |
| 4,873,921 A | 10/1989 | Piane, Sr. |
| D306,645 S | 3/1990 | Parker |
| 4,915,688 A | 4/1990 | Bischof et al. |
| 4,915,689 A | 4/1990 | Theeuwes |
| 4,970,053 A | 11/1990 | Fechtner |
| 5,005,721 A | 4/1991 | Jordan |
| 5,009,309 A | 4/1991 | Hansen |
| 5,037,390 A | 8/1991 | Raines et al. |
| 5,040,678 A | 8/1991 | Lenmark, Sr. et al. |
| 5,061,264 A | 10/1991 | Scarrow |
| 5,117,997 A | 6/1992 | Fink |
| 5,148,919 A | 9/1992 | Rubin |
| 5,304,165 A | 4/1994 | Haber et al. |
| 5,322,668 A | 6/1994 | Tomasso |
| D355,260 S | 2/1995 | Tomasso |
| 5,431,509 A | 7/1995 | Anderson et al. |
| 5,465,841 A | 11/1995 | Wilson et al. |
| 5,582,222 A | 12/1996 | Riall |
| 5,609,248 A | 3/1997 | Rohrbough et al. |
| 5,725,499 A | 3/1998 | Silverstein et al. |
| 5,785,701 A | 7/1998 | Sams et al. |
| 5,836,910 A | 11/1998 | Duffy et al. |
| 5,873,731 A | 2/1999 | Prendergast |
| 5,897,526 A | 4/1999 | Vaillancourt |
| 5,941,846 A | 8/1999 | Duffy et al. |
| 5,954,213 A | 9/1999 | Gerhart et al. |
| 5,954,313 A | 9/1999 | Ryan |
| 5,957,313 A | 9/1999 | Bouan |
| 5,989,237 A | 11/1999 | Fowles et al. |
| 6,000,548 A | 12/1999 | Tsals |
| 6,022,339 A | 2/2000 | Fowles et al. |
| 6,102,232 A | 8/2000 | Lin et al. |
| 6,102,233 A | 8/2000 | Waugh |
| 6,164,450 A | 12/2000 | Benedetti |
| 6,213,529 B1 | 4/2001 | Kurcz et al. |
| 6,305,541 B1 | 10/2001 | Tanner et al. |
| D457,949 S | 5/2002 | Krug et al. |
| 6,474,375 B2 | 11/2002 | Spero et al. |
| 6,508,791 B1 | 1/2003 | Guerrero |
| 6,558,628 B1 | 5/2003 | Reo |
| 6,613,283 B2 | 9/2003 | Reo |
| 6,641,565 B1 | 11/2003 | Lavi et al. |
| 6,789,828 B1 | 9/2004 | Borg |
| 6,929,474 B2 | 8/2005 | Schenck et al. |
| 7,074,205 B1 | 7/2006 | Duffy et al. |
| 7,214,210 B2 | 5/2007 | Kamen et al. |
| 7,442,181 B2 | 10/2008 | Schubert et al. |
| 7,468,049 B2 | 12/2008 | Laveault |
| 7,553,291 B2 | 6/2009 | Duffy et al. |
| 7,607,541 B2 | 10/2009 | Girgis et al. |
| D620,603 S | 7/2010 | Talmer et al. |
| 7,798,997 B2 | 9/2010 | Kamen et al. |
| 7,819,342 B2 | 10/2010 | Spallek et al. |
| D632,802 S | 2/2011 | Salinas et al. |
| 7,935,076 B2 | 5/2011 | Estes et al. |
| D645,973 S | 9/2011 | Hoenes |
| 8,425,487 B2 | 4/2013 | Beiriger et al. |
| 8,545,440 B2 | 10/2013 | Patrick et al. |
| 8,652,097 B2 | 2/2014 | Lee |
| 8,684,433 B2 | 4/2014 | Oesterle et al. |
| 8,790,328 B2 | 7/2014 | Kragelund et al. |
| 8,968,244 B2 | 3/2015 | Kamen et al. |
| 9,132,061 B2 | 9/2015 | Beiriger |
| D769,456 S | 10/2016 | Dulaff |
| D778,460 S | 2/2017 | Marechal et al. |
| D847,634 S | 5/2019 | Hatakeyama |
| D847,974 S | 5/2019 | McNall et al. |
| D865,993 S | 11/2019 | Trump et al. |
| D886,611 S | 6/2020 | Jones et al. |
| D890,358 S | 7/2020 | Jones et al. |
| D893,046 S | 8/2020 | Jones et al. |
| D902,428 S | 11/2020 | Klintstedt et al. |
| 11,684,548 B2 | 6/2023 | Schweiss et al. |
| 11,903,900 B2 | 2/2024 | Jones et al. |
| 2001/0009994 A1 | 7/2001 | Small et al. |
| 2002/0004643 A1 | 1/2002 | Carmel et al. |
| 2002/0104584 A1 | 8/2002 | Spero et al. |
| 2003/0107628 A1 | 6/2003 | Fowles et al. |
| 2004/0241041 A1 | 12/2004 | Woodworth et al. |
| 2004/0260266 A1 | 12/2004 | Cuschieri et al. |
| 2005/0045495 A1 | 3/2005 | Dalsing et al. |
| 2005/0126653 A1 | 6/2005 | Tachikawa et al. |
| 2005/0175338 A1 | 8/2005 | Ide et al. |
| 2007/0005020 A1 | 1/2007 | Laveault |
| 2007/0267378 A1 | 11/2007 | Piccinino et al. |
| 2007/0278245 A1 | 12/2007 | Brooks et al. |
| 2009/0062732 A1 | 3/2009 | Radmer |
| 2009/0099547 A1 | 4/2009 | Radmer |
| 2009/0182300 A1 | 7/2009 | Radmer et al. |
| 2010/0022974 A1 | 1/2010 | Sharratt et al. |
| 2012/0029464 A1 | 2/2012 | Kragelund et al. |
| 2012/0053555 A1 | 3/2012 | Ariagno et al. |
| 2012/0089088 A1 | 4/2012 | Foshee et al. |
| 2012/0127824 A1 | 5/2012 | Petrone |
| 2012/0298254 A1 | 11/2012 | Brem et al. |
| 2013/0046270 A1 | 2/2013 | Foshee et al. |
| 2013/0284735 A1 | 10/2013 | Oesterle et al. |
| 2014/0021076 A1 | 1/2014 | Soma et al. |
| 2015/0005734 A1 | 1/2015 | Inoue et al. |
| 2015/0166212 A1 | 6/2015 | Wissner et al. |
| 2016/0015889 A1 | 1/2016 | Caquias et al. |
| 2016/0081308 A1* | 3/2016 | Cary ............... A61M 5/162 222/80 |
| 2016/0266156 A1 | 9/2016 | Brennan et al. |
| 2017/0020784 A1 | 1/2017 | Schweiss et al. |
| 2020/0155413 A1 | 5/2020 | Schweiss et al. |
| 2020/0170884 A1 | 6/2020 | Tashjian |

(56) References Cited

U.S. PATENT DOCUMENTS

| | | |
|---|---|---|
| 2021/0172923 A1 | 6/2021 | Kaufman et al. |
| 2021/0369566 A1 | 12/2021 | Jones et al. |

FOREIGN PATENT DOCUMENTS

| | | |
|---|---|---|
| CN | 101370534 A | 2/2009 |
| CN | 102387827 A | 3/2012 |
| CN | 202184989 U | 4/2012 |
| CN | 202236710 U | 5/2012 |
| CN | 102711710 A | 10/2012 |
| CN | 102958455 A | 3/2013 |
| CN | 103402481 A | 11/2013 |
| CN | 103990201 A | 8/2014 |
| CN | 106413661 A | 2/2017 |
| CN | 206045076 U | 3/2017 |
| CN | 206120865 U | 4/2017 |
| CN | 108040465 A | 5/2018 |
| CN | 108093623 A | 5/2018 |
| CN | 207591040 U | 7/2018 |
| CN | 108366904 A | 8/2018 |
| CN | 108602591 A | 9/2018 |
| CN | 201830503853.6 | 9/2018 |
| CO | 7061051 A2 | 9/2014 |
| CO | 14277741 | 12/2014 |
| DE | 202009012540 U1 | 10/2010 |
| EP | 0 495 808 B1 | 7/1992 |
| EP | 0 631 816 A1 | 1/1995 |
| EP | 0 734 963 B1 | 10/1996 |
| EP | 3 569 216 A1 | 11/2019 |
| FR | 2 085 307 A1 | 12/1971 |
| FR | 2 715 131 A1 | 7/1995 |
| JP | 08-324571 A | 12/1996 |
| JP | 2002-011097 A | 1/2002 |
| JP | 3142209 U | 6/2008 |
| JP | 2012-528692 A | 11/2012 |
| JP | D1463610 | 3/2013 |
| JP | 2013-515925 A | 5/2013 |
| JP | 2013-536049 A | 9/2013 |
| JP | 2014-504921 A | 2/2014 |
| JP | 2015-503964 A | 2/2015 |
| JP | 2015-509421 A | 3/2015 |
| JP | D2016-11117 | 5/2016 |
| JP | 2018-519141 A | 7/2018 |
| RU | 2136326 C1 | 9/1999 |
| RU | 2554852 C2 | 6/2015 |
| TW | 455382 | 9/2001 |
| TW | 201707670 A | 3/2017 |
| TW | D194378 | 12/2018 |
| WO | WO 93/01739 A1 | 2/1993 |
| WO | WO 94/27669 A1 | 12/1994 |
| WO | WO 1996/032917 A1 | 10/1996 |
| WO | WO 99/27886 A1 | 6/1999 |
| WO | WO 03/054552 A2 | 7/2003 |
| WO | WO 2004/032808 A2 | 4/2004 |
| WO | WO 2009/083347 A1 | 7/2009 |
| WO | WO 2010/043683 A1 | 4/2010 |
| WO | WO 2010/141632 A2 | 12/2010 |
| WO | WO 2011/079225 A1 | 6/2011 |
| WO | WO 2012/102216 A1 | 8/2012 |
| WO | WO 2013/126055 A1 | 8/2013 |
| WO | WO 2013/162959 A1 | 10/2013 |
| WO | WO 2015/006822 A1 | 1/2015 |
| WO | WO 2016/011450 A1 | 1/2016 |
| WO | WO 2016/152016 A1 | 9/2016 |
| WO | WO-2016/205687 * | 12/2016 |
| WO | WO 2016/205687 A1 | 12/2016 |

OTHER PUBLICATIONS

International Search Report and Written Opinion mailed Jun. 24, 2020 in connection with International Application No. PCT/US2019/052572.

International Preliminary Report on Patentability mailed Apr. 15, 2021 in connection with International Application No. PCT/US2019/052572.

International Search Report and Written Opinion mailed Aug. 17, 2016 in connection with International Application No. PCT/US2016/038136.

International Preliminary Report on Patentability mailed Dec. 28, 2017 in connection with International Application No. PCT/US2016/038136.

Extended European Search Report dated Aug. 6, 2019 in connection with European Application No. 19169568.3.

Chinese Office Action issued Jan. 16, 2020 with English translation in connection with Chinese Application No. 201680035766.0.

Columbian Office Action dated Jul. 26, 2019 and English summary thereof in connection with Columbian Application No. NC2017/0012908.

U.S. Appl. No. 18/316,151, filed May 11, 2023, Schweiss et al.

International Search Report and Written Opinion mailed Jul. 26, 2013 in connection with International Application No. PCT/US2013/0368769.

International Preliminary Report on Patentability mailed Nov. 6, 2014 in connection with International Application No. PCT/US2013/036879.

Invitation to Pay Additional Fees mailed Jan. 9, 2020 in connection with International Application No. PCT/US2019/052574.

International Search Report and Written Opinion mailed Mar. 2, 2020 in connection with International Application No. PCT/US2019/052574.

International Preliminary Report on Patentability mailed Apr. 15, 2021 in connection with International Application No. PCT/US2019/052574.

Tractor S.C. Online. Published date unkown. Retrieved on Jan. 9, 2020 from URL: https://en.wikipedia.org/wiki/Tractor_S.C.

* cited by examiner

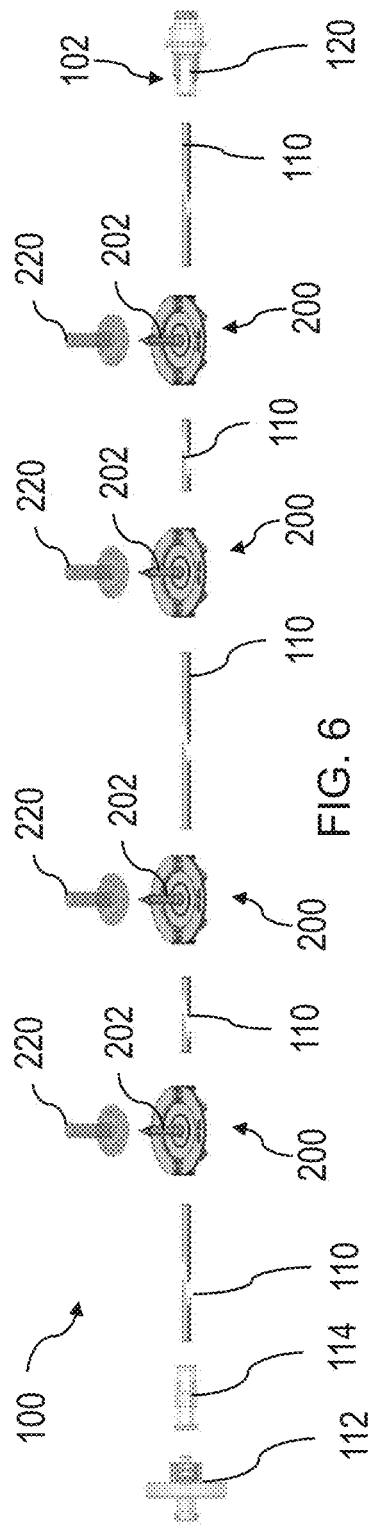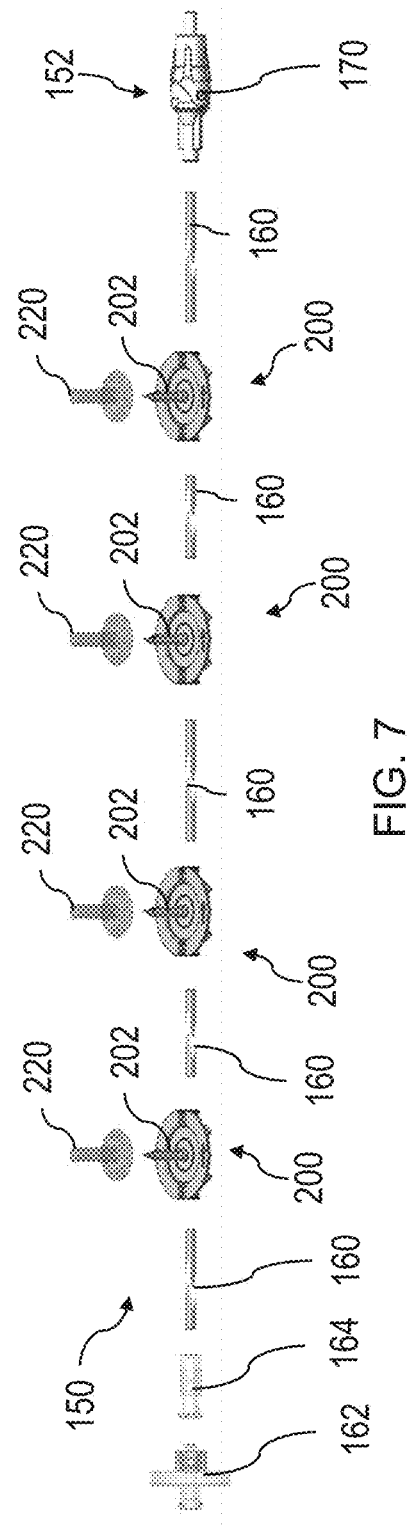

POOLING DEVICE FOR SINGLE OR MULTIPLE MEDICAL CONTAINERS

CROSS-REFERENCE TO RELATED APPLICATIONS

This application is a national stage filing under 35 U.S.C. § 371 of International Patent Application Serial No. PCT/US2019/052572, filed on Sep. 24, 2019, which claims the benefit under 35 U.S.C. § 119 (e) of U.S. Provisional Application No. 62/819,349, filed on Mar. 15, 2019, and U.S. Provisional Application No. 62/740,475, filed on Oct. 3, 2018, each of which is incorporated herein by reference in its entirety.

FIELD

Disclosed embodiments are related to a pooling device for pooling medicinal fluids from single or multiple medical containers.

BACKGROUND

Medicinal fluids are often manufactured and packaged separately prior to use to preserve their chemical and physical stability. The medicinal fluids may be combined during administration, either by mixing the medicinal fluids immediately prior to administration or by administering the medicinal fluids concurrently or sequentially.

Typically, these additional steps during administration are performed by a nurse or other medical professional, who may need to follow a specialized procedure to administer the medicinal fluids to a patient. In cases where additional medicinal fluids are needed, the method of administration may be performed by the nurse or other medical professional multiple times for a predetermined dosage.

Conventional administration methods and systems may lack a streamlined procedure and may require many steps connecting and disconnecting components and moving fluid through various components in a specific manner. The inventors have recognized the need for a medicinal pooling system that streamlines administration of medicinal fluid to a patient.

SUMMARY

In some embodiments, systems and methods for administering a medicinal fluid to a patient from one or more containers are provided. In some embodiments, a medicinal fluid pooling device includes a hollow spike configured to pierce and receive fluid from a medicinal fluid container, where the spike includes portions of different cross-sectional area to facilitate sealing with an associated spike sheath. In some embodiments, a hollow spike of a medicinal fluid pooling device is part of a port, and the port has an associated cover that removably connects with the port to cover the hollow spike. In some embodiments, a medical device may include a fluidic interface having a housing that contains at least a portion of a fluidic connector that includes a luer activated valve.

In one embodiment, a medicinal fluid pooling device includes a spike sheath, a spike having a body including a first body portion and a second body portion, tubing in fluidic communication with the internal channel of the spike, and a base coupled to the spike. The first body portion and second body portion have different cross sectional shapes, where the second body portion is configured to create a fluidic seal with the spike sheath. An internal channel extends through the first body portion and the second body portion. The spike sheath is configured to compress and move towards the base when a force is applied to the spike sheath in a direction toward the base.

In another embodiment, a fluidic interface of a medical device includes a fluidic connector including a first end, a second end, and a luer activated valve controlling fluidic communication between the first end and the second end, tubing in fluidic communication with the second end, and a housing including a first aperture and a second aperture. The housing contains at least a portion of the fluidic connector, wherein the first end of the fluidic connector is accessible.

In another embodiment, a medicinal fluid pooling device includes a port including a hollow spike, tubing in fluidic communication with the hollow spike, and a cover configured to removably connect to the port to cover the hollow spike.

In one embodiment, a method of using a pooling device for pooling a medicinal fluid includes removing a cover to expose a port of the pooling device, the port including a hollow spike and a spike sheath covering the spike, connecting a first container to the port by pushing the first container onto the spike, causing the spike sheath and the first container to be pierced by the spike to allow fluidic communication between an internal volume of the first container and the spike, and coupling an infusion pump to the tubing to cause the medicinal fluid to move through the tubing and into a patient. The spike sheath forms a seal against the spike prior to insertion of the first container into the port. The internal volume of the first container contains medicinal fluid, and the spike is in fluidic communication with tubing.

In another embodiment, a wearable fluid pooling device includes a housing including a clip configured to allow the wearable fluid pooling device to couple to clothing, a first port formed in the housing and configured to receive a first container, and a first spike disposed in the first port and configured to pierce the first container when the first port receives the first container.

In another embodiment, wearable fluid pooling system includes a first wearable fluid pooling device. The first wearable pooling device includes a first housing including a first clip configured to allow the first wearable fluid pooling device to couple to clothing, a first port formed in the first housing and configured to receive a first container, a first spike disposed in the first port and configured to pierce the first container when the first port receives the first container, a first fluidic outlet connector configured to be fluidly connected to an associated device to allow fluid communication between the first wearable fluid pooling device and the associated device, a fluidic inlet connector, and first tubing connected to the first spike, first fluidic outlet connector, and fluidic inlet connector. The first tubing is configured to allow fluid communication between the fluidic inlet connector, first spike, and first fluidic outlet connector. The wearable fluid pooling system also includes a second wearable fluid pooling device. The second wearable fluid pooling device includes a second housing including a second clip configured to allow the second wearable fluid pooling device to couple to clothing, a second port formed in the second housing and configured to receive a second container, a second spike disposed in the second port and configured to pierce the second container when the second port receives the second container, a second fluidic outlet connector configured to be fluidly coupled to the first fluidic inlet connector to allow fluid communication between the second wearable fluid pooling device and the first wearable fluid pooling device, and second tubing connected to the second spike and the second fluidic outlet connector. The second tubing is configured to allow fluid communication between the second fluidic outlet connector and the second spike.

In another embodiment, a method for administering a medicinal fluid to a patient includes connecting a first container to a first port formed in a first housing by pushing the first container onto a first spike disposed in the first port, causing the first container to be pierced by the first spike to allow fluidic communication between the first spike and an internal volume of the first container, where the internal volume of the first container contains a medicinal fluid. The method may also include connecting an infusion set to a first fluidic outlet connector which allows fluidic communication between the infusion set and the internal volume of the first container via the first spike, venting air disposed in the infusion set, and drawing the medicinal fluid from the internal volume of the first container into the infusion set.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 6 is an exploded view of the first fluid distribution system of FIG. 3;

FIG. 7 is an exploded view of the second fluid distribution system of FIG. 4;

DETAILED DESCRIPTION

Figure 1:
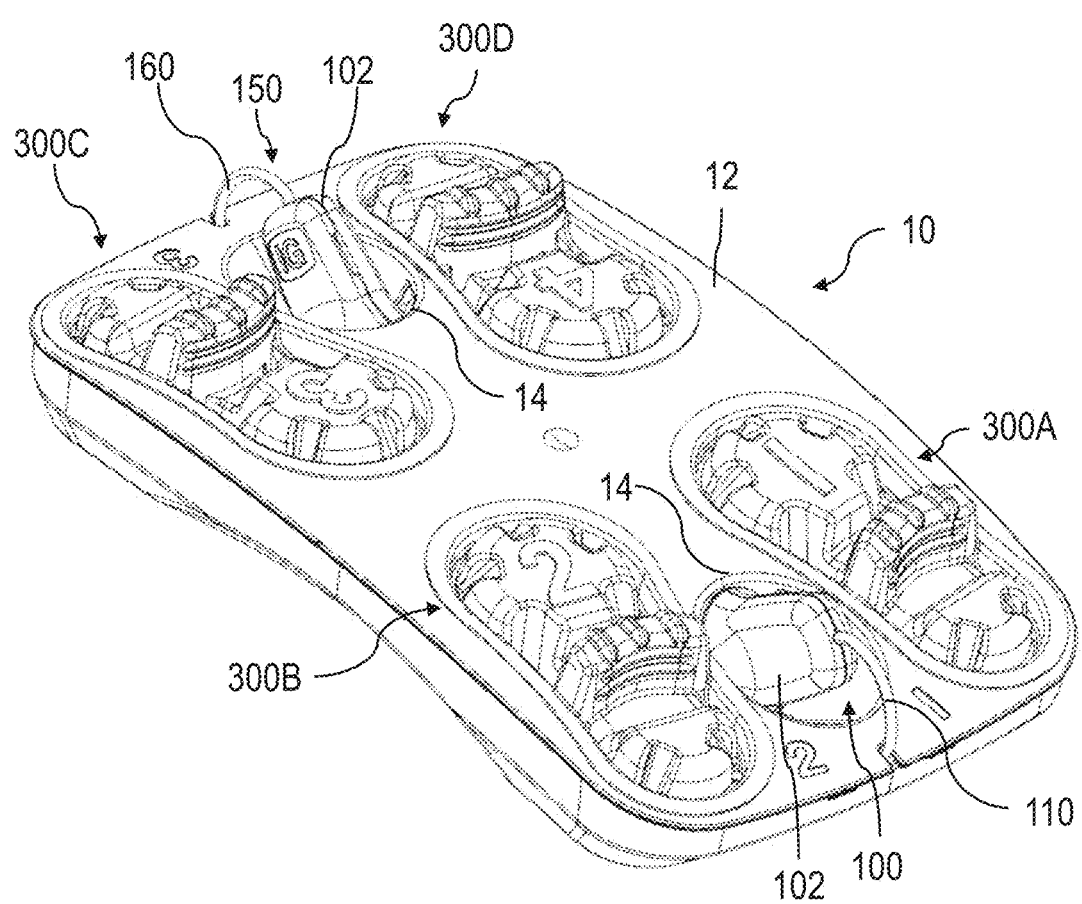
FIG. 1 is a perspective view of one embodiment of a medicinal pooling device.

During a typical administration process, multiple syringes may be used to mix medicinal fluids in a series of steps prior to injection into a patient. At each step, a nurse or other medical professional takes care to ensure sterility as the individual fluids are withdrawn from their packaging and expelled into a mixing container. Even if the medicinal fluids do not need to be pre-mixed prior to injection into a patient, each fluid is typically withdrawn individually by a pump, syringe, or other suitable tool. If a dosage larger than that contained in a typical package is required for a particular patient, the process is typically repeated multiple times until the required dosage is reached. Accordingly, conventional administration methods performed by nurses or medical professionals can be time consuming and complicated.

In some cases, due to the frequency of treatment using some medicinal fluids, self-administration is a preferable option for convenience and cost. Difficult procedures which are already time consuming when performed by medical professionals can be challenging for a patient practicing self-administration. Accordingly, reducing the time consumption and complexity of medicinal fluid administration is desirable to patients who self-administer for convenience and a reduced impact on day-to-day life.

In view of the above, the inventors have recognized the benefits of a medicinal pooling device which allows a patient to administer medicinal fluids contained in one or more containers. As compared to a conventional administration process, the pooling device may enable the use of a simpler medicinal fluid administration process having less steps. The pooling device may also allow for administration of an increased dosage using multiple containers of medicinal fluid so that the steps of an administration process may be performed once for a predetermined dosage.

The inventors have also recognized the benefits of a spike and spike sheath which allows for a simple, sterile connection between a container of medicinal fluid and a medicinal pooling device. The spike sheath may be broken by the container as the container is inserted into the medicinal pooling device to start pooling and fluid flow to a patient device (e.g., infusion pump, syringe, etc.). Accordingly, a patient does not need to pierce a container using a handheld syringe or other tool which may be cumbersome or present sterility problems.

In some embodiments, a medicinal fluid pooling device includes at least one port with a spike. The spike may include a first body portion and a second body portion, where the first body portion and second body portion have different cross sectional shapes. That is, the spike may transition from a body portion with a first shape to a body portion with a second shape along the length of the spike. The second body portion may have a shape configured to create a fluidic seal with a spike sheath. The spike sheath may have a shape complementary to that of the second body portion, so that the spike sheath may create a fluidic seal around the spike when the spike is received by the sheath. The spike may include an internal channel extending through the length of the spike, so that the medicinal fluid pooling device may be in fluid communication with a medicinal fluid container one the container is received by the port. The spike may be connected to tubing which allows the transfer of medicinal fluid to a patient device. The spike sheath may seal off the spike until the container is received, whereupon the sheath may be broken and compressed by the container, thereby keeping the spike sterile until connection with the container.

The inventors have also recognized the benefits of a fluidic interface which allows for easy connection of a patient device such as an infusion pump or a syringe. Typically, medical grade fluid connection devices (e.g., luer activated connectors) are small and difficult to grasp or otherwise manipulate for self-administration of medicinal fluids. Accordingly, a fluidic interface that is sized and shaped to be easier to grasp may simplify and improve the administration of medicinal fluids.

In some embodiments, a fluidic interface includes a fluidic connector and a housing. The housing may include first and second apertures configured to provide access to an internal volume of the housing. The fluidic connector may have a first end and a second end, where the first end is configured to be coupled to a patient device and the second end is connected to tubing configured to carry medicinal fluid (e.g., from a medicinal pooling device). The fluidic connector may be disposed and mounted in the internal volume of the housing, which may have a size and shape to increase ease of grasping and movement of the housing by an operator. Accordingly, the housing may facilitate medicinal fluid administration processes for a patient or medical professional.

The inventors have also recognized the benefits of a removable cover for a medicinal pooling device which allows a patient to selectively access ports to connect containers of medicinal fluids. A cover may provide a simple way of communicating administration steps or other information to a patient for self-care, as well as provide protection for any sterile components used to connect the containers.

In some embodiments, a medicinal pooling device includes at least one port, where each port includes at least one spike assembly. The ports may be recessed into the pooling device, so that the spike assemblies do not protrude out of the outermost extremities of the pooling device. Each port of the medicinal pooling device may have an associated cover configured to cover the at least one spike disposed in the port so that the at least one spike is inaccessible prior to removable of the cover. The cover may be removably connectable to the at least one port, so that a patient or a medical professional may remove the cover during an administration process for medicinal fluids.

In some embodiments, a medicinal fluid pooling device includes a housing with a plurality of ports and at least one fluid distribution system disposed therein. The plurality of ports may include spikes or other connectors suitable to fluidly connect one or more containers of medicinal fluid to the at least one fluid distribution system. The ports may include multiple spikes which may be used to fluidly connect multiple containers packaged together in a container unit. The fluid distribution system may include an air filter, tubing, and a fluidic connector of a fluidic interface used to withdraw fluid from the one or more containers once they have been fluidly connected to the fluid distribution system. The ports may be configured to receive the one or more containers in an inverted position so that gravity may be used to supply the medicinal fluid at the fluidic connector. The fluid distribution system may supply a single medicinal fluid from multiple containers connected to different ports, or may supply a mixture of different medicinal fluids connected to different ports. The air filter may allow air into the fluidic distribution system to replace any volume of fluid withdrawn from the fluidic connector. The fluidic connector may be configured to connect to any patient device that may be used to administer fluid to a patient, such as an infusion pump or syringe. Prior to insertion of the one or more containers, the plurality of ports may be enclosed with a cover which may be removed by a patient or medical professional prior to the connection of a container to a port.

In some embodiments, a method for administering a medicinal fluid using a medicinal pooling device includes removing one or more covers to expose one or more ports of the pooling device, connecting one or more containers of medicinal fluid to the one or more ports, and coupling a patient device to a fluidic connector of a fluid distribution system to withdraw the medicinal fluid from the one or more containers. The ports of the medicinal pooling device may include one or more spike assemblies, each spike assembly including a hollow spike and a spike sheath covering the spike. When the cover is removed and the spike assemblies are exposed, connecting a container to a spike may include pushing the container onto the spike, causing the spike sheath and the container to be pierced by the spike to allow fluidic communication between the spike and an internal volume of the container. In some embodiments, the spike sheath may form a seal against the spike to promote transfer of medicinal fluid from the connected container to the spike rather than allowing the fluid to leak out of the container outside of the fluid distribution system. Once a container is connected, medicinal fluid from the container may flow through the spike and coupled tubing to the fluidic connector which may be used to connect the fluid distribution system to an infusion pump, syringe, or other device for administration into a patient. If more than one container is connected to the fluidic distribution system, the total volume of fluid in each of the containers may be combined and delivered as a single volume at the fluidic connector. In some embodiments, multiple fluid distribution systems may be used in the medicinal pooling device to deliver different medicinal fluids or to provide a mixture of different medicinal fluids.

In some embodiments, the medicinal pooling device may be used to administer two or more medicinal fluids in sequence. For example, a first fluid may be administered initially to improve the conditions under which the second fluid is delivered to or processed by the patient. In some embodiments, the medicinal pooling device may be used with one or more container units that hold two or more containers together, each container holding a different medicinal fluid. An example of a dual medical container unit that may be used with the medicinal pooling device is described in U.S. Pat. No. 8,684,433, entitled "PACKAGING FOR MULTIPLE MEDICAL CONTAINERS," filed with the U.S. Patent and Trademark Office on Apr. 26, 2012, and incorporated herein by reference. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

The inventors have also recognized the benefits of a pooling device which may be wearable to allow a patient free mobility during a fluid administration process. The wearable pooling device may be coupled to clothing or otherwise secured to a patient so the patient is not restricted to a specific position, location, or region. The wearable pooling device may also include a lid configured to secure one or more attached containers to the pooling device such that movement of the patient does not disturb the fluid administration process. Such an arrangement may greatly reduce the burden of performing an infusion or other administration process for a patient by providing free mobility without detriment to the administration process.

In some embodiments, a wearable pooling device includes a housing having a clip. The housing may include one or more ports formed in the housing configured to receive one or more containers of medicinal fluid to be administered during an infusion process. The housing, ports, and clip may be arranged so that the housing and attached containers of medicinal fluid may be suspended from a patient. In some embodiments, the clip may be configured as a belt clip configured to releasably attach the housing to a belt worn by the patient. In other embodiments, the clip may be configured as a harness, strap, or other suitable configuration for securing the housing and attached one or more containers to the patient. In some embodiments, the housing may include a lid which is movable between a closed position, where the one or more ports and enclosed, and an open position, where the one or more ports are accessible. According to this embodiment, the lid may be closed when one or more containers are disposed in the one or more ports so that the containers are reliably secured inside of the ports. Such an arrangement may prevent jostling, bumps, or other dynamic motion common during daily activities from dislodging the one or more containers or otherwise interrupting an administration process.

The inventors have also recognized the benefits of a modular pooling device which allows multiple pooling devices to be coupled together to increase the total volume of fluid pooled. In some cases, manufacturing, regulatory, or other constraints may limit the size of a container which may be employed with a pooling device. Accordingly, in some embodiments, a pooling device may be connectable to other pooling devices to increase the total volume of fluid and/or total number of containers available for an administration process.

In some embodiments, a modular pooling device includes a fluidic inlet connector and a fluidic outlet connector. The fluidic inlet connector and the fluidic outlet connector may be connectable to one another to bring multiple modular pooling devices into fluidic communication with one another. In some embodiments, the fluidic inlet connector and the fluidic outlet connector may be connected with tubing. In this embodiment, the tubing may provide freedom of movement of the connected pooling devices. Such an arrangement may be beneficial in wearable applications where multiple smaller pooling devices may be easier to wear than a single bulky pooling device. In other embodiments, the fluidic inlet connector and fluidic outlet connector may be directly connectable to one another. According to this embodiment, the connected pooling devices may be fluidly connected and physically connected to reduce the number of structures which are independently manipulable, which may simplify moving and/or wearing the connected pooling devices.

The inventors have also recognized the benefits of an infusion set which can vent air so that the infusion set may be used sequentially with multiple pooling devices. In some cases, it may be desirable to disconnect a first pooling device and connect a second pooling device to complete an infusion process while using the same infusion set to deliver medicinal fluid to the patient. For example, the volume of fluid deliverable from a single pooling device may be insufficient for some dosages. Accordingly, in such cases, it may be desirable to connect another pooling device safely if an additional volume of fluid is prescribed. The infusion set may include a breather valve (i.e., degassing valve, air release valve, etc.) configured to prevent air bubbles which may form during the transition between pooling devices from being administered to the patient.

In some embodiments, an infusion set includes tubing having a breather valve and a needle set having at least one needle for delivering medicinal fluid to a patient. The infusion set may include an inlet connector which allows the infusion set to be coupled to a pooling device either directly (e.g., to a fluidic outlet connector of the pooling device) or indirectly (e.g., via an infusion pump, regulator, or other device). Once connected to the pooling device, the degassing valve may allow air to flow out of the tubing to allow medicinal fluid from the pooling device to replace said air. Accordingly, air will be removed from the tubing of the infusion set before administration to the patient. Any additional air bubbles which form may also be removed from the tubing by the breather valve.

According to exemplary embodiments described herein, a pooling device and infusion set may be used with any number of medicinal or nutritional fluids which are delivered to the body (e.g., subcutaneously). In some embodiments, a pooling device and infusion set may be configured to pool and deliver Immune Globulin Infusion 10% (Human), Immune Globulin Subcutaneous (Human) 20% (e.g., CUVITRU), Recombinant Human Hyaluronidase (e.g., HYQVIA), and/or other blood products. Without wishing to be bound by theory, pooling devices of exemplary embodiments herein may be configured to deliver medicinal fluids having viscosity between 10 and 30 cP. Of course, a pooling device, infusion set, and associated accessories may be employed with any desirable medicinal fluid, as the present disclosure is not so limited.

Although a particular embodiment of the present pooling device will be described herein, other alternate embodiments of all components related to the present pooling device are interchangeable to suit different applications. The term "pooling device" as used in this application refers to a device for accessing the medicinal fluid from one or more medical containers for administering the medicinal fluid to a patient. Thus, a pooling device used to administer medicinal fluid from a single container is contemplated, as well as several medical containers.

FIG. 1 depicts one embodiment of a medicinal pooling device 10. The medicinal pooling device includes a housing 12, a first fluid distribution system 100, a second fluid distribution system 150, and four covers 300A, 300B, 300C, 300D each covering a port for receiving a container of medicinal fluid. In the embodiment depicted in FIG. 1, the medicinal pooling device is configured to supply two medicinal fluids that may be pooled from up to four containers for each fluid. The first medicinal fluid may be packaged with the second medicinal fluid, such that each port may receive both medicinal fluids simultaneously. According to the present embodiment, the medicinal fluids are not mixed, but are rather supplied independently to a first fluidic interface 102 and a second fluidic interface 152, and may be delivered sequentially to a patient. The first and second medicinal fluids may be carried by a first tubing 110 and a second tubing 160 to the first and second fluidic interfaces, respectively. As shown in FIG. 1, the first and second fluidic interfaces may be removably connected to interface holders 14 for storage and transportation.

In some cases, it may be desirable to maintain the cleanliness of a medicinal pooling device using a predetermined manufacturing and shipping orientation. According to the embodiment shown in FIG. 1, the medicinal pooling device 10 may keep important components that may interface with medicinal fluid covered or otherwise protected from an external environment. For example, the covers 300A, 300B, 300C, 300D may keep the at least one spike assembly disposed therein isolated from external contaminants and accidental damage that may be encountered by the medicinal pooling device during shipping and handling prior to use. The covers may also inhibit the operator from contacting the spikes while handling the medicinal pooling device prior to, during, and/or after use of medicinal pooling device. Similarly, the interface holders 14 may orient the first and second fluidic interfaces 102, 152, in a manner to protect any exposed end of the first fluid distribution system 100 and second fluid distribution system 150. Of course, any suitable components may be used to protect the sterility of the medicinal pooling device prior to first use, including, but not limited to, plastic sheathing or other sterile packaging.

Figure 2:
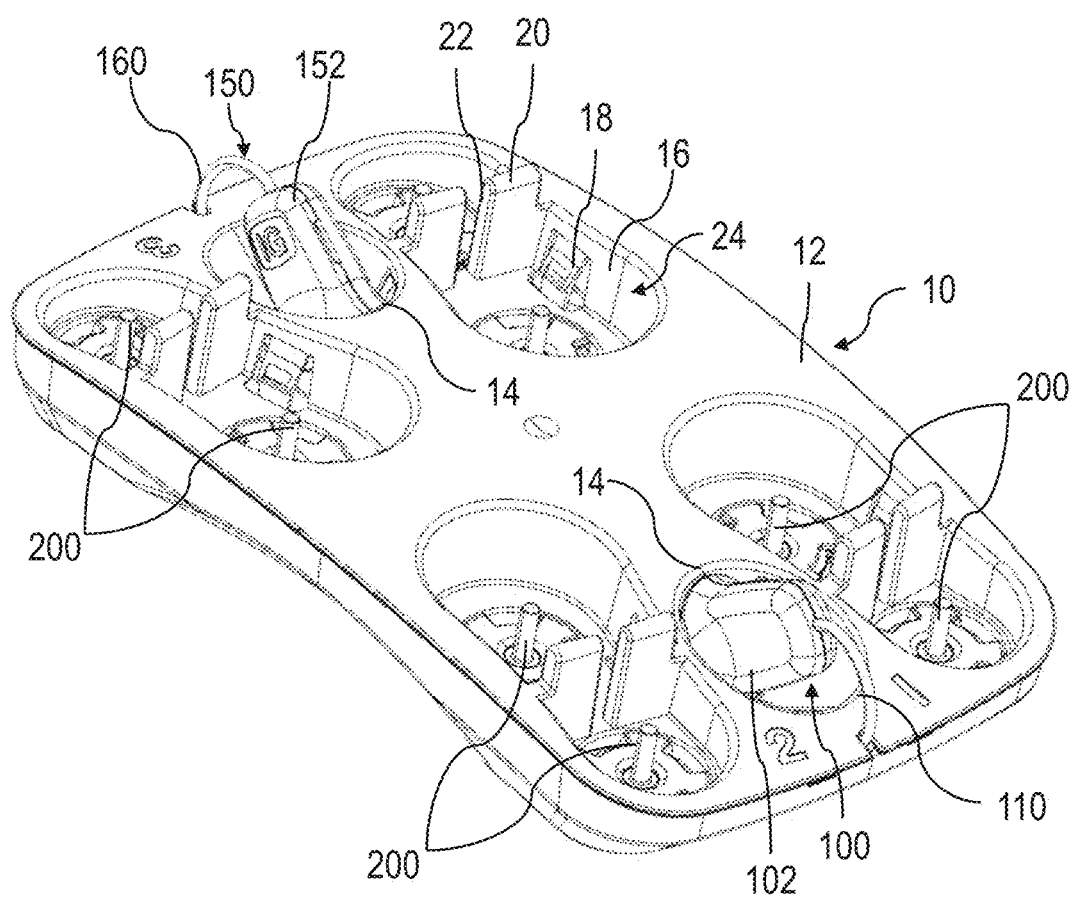
FIG. 2 is a perspective view of the medicinal pooling device of FIG. 1 with covers removed.

FIG. 2 shows the medicinal pooling device 10 of FIG. 1 with covers 300A, 300B, 300C, 300D removed. With the covers removed, the ports 24 of the medicinal pooling device are exposed. Each port includes a recess 16 configured to receive a container of medicinal fluid for pooling and/or administration to a patient. As shown in FIG. 2, each port includes two spike assemblies 200. In each port, one spike assembly is connected to the first fluid distribution system 100 and one spike assembly is fluidly connected to the second fluid distribution system 150. Accordingly, each port may accommodate multiple containers of separate medicinal fluids for pooling and administration. In the embodiment shown in FIG. 2, when the medicinal fluid containers are inserted into the ports, the containers may be pierced by one of the spike assemblies 200 to fluidly connect the container to one of the fluid distribution systems 100, 150.

As shown in FIG. 2, each port 24 may include components configured to align inserted containers, promote sterility, or otherwise simplify the medicinal administration process. For example, the ports may include a recess 16 form in the housing 12 of the medicinal pooling device, allowing a container of medicinal fluid to be guided by the port as the container is pushed onto spike assembly 200 by a patient or medical professional. That is, a medicinal fluid container with a perimeter shape complementary to that of the perimeter of the port may be aligned and guided automatically as the container is pressed onto the spike assembly. The port may also include a guide projection 20 and a guide slot 22 configured to provide additional guiding and aligning surfaces for insertion of the medicinal fluid containers. In some embodiments, two containers of medicinal fluid may be physically coupled by a housing to form a single container unit. Accordingly, the guide projection and guide slot may contact portions of the container unit housing to reliably guide and align the individual containers disposed therein with the spike assemblies 200. In the embodiment shown in FIG. 2, the port includes at least one latch receptacle 18 configured to removably connect the covers (covers 300A, 300B, 300C, and 300D shown in FIG. 1) to the medicinal pooling device. The latch receptacle 18 may also be used to removably or permanently couple any received container or container unit in the port to inhibit removal. As such, in some embodiments, the latch receptacles of the medicinal pooling device may be configured to removably couple with an associated port cover and permanently couple with an associated container. In some embodiments, the latch receptacles may be configured to removably couple with both the port covers and the containers. The ports may include any suitable alignment features or locking features, as the present disclosure is not so limited.

In some embodiments, a port may include any suitable fluidic coupler that may be used to connect a container of medicinal fluid to a fluid distribution system of a medicinal pooling device. For example, the port may include a spike or quick connect couplers. In some embodiments, a port may also include a recess and/or projection formed in a housing of a medicinal pooling device. The recess and/or projection may be used to facilitate alignment and connection of the container to the port. In other embodiments, a port may be flush with a housing of the medicinal pooling device. A port may have any other suitable arrangement for fluidly connecting a container to the fluid distribution system of a medicinal pooling device, as the present disclosure is not so limited.

In some cases, it may be desirable to maintain the sterility of the medicinal pooling device by inhibiting subsequent uses of the pooling device. Accordingly, in some embodiments, a medicinal pooling device may be configured for single use as a disposable device. That is, the medicinal pooling device may be configured to discourage or prevent reuse of the medicinal pooling device. For example, as shown in FIG. 2, the latch receptacles 18 of the medicinal pooling device 10 may be configured to substantially prevent removal of a container attached to a port 24. Thus, an operator (e.g., patient or medical professional) may not be able to replace a container of medicinal fluid to begin a second administration process. It should be appreciated that any other suitable component may be used to inhibit multiple uses of the pooling device, including mechanical lockouts and self-closing valves.

Figure 3:
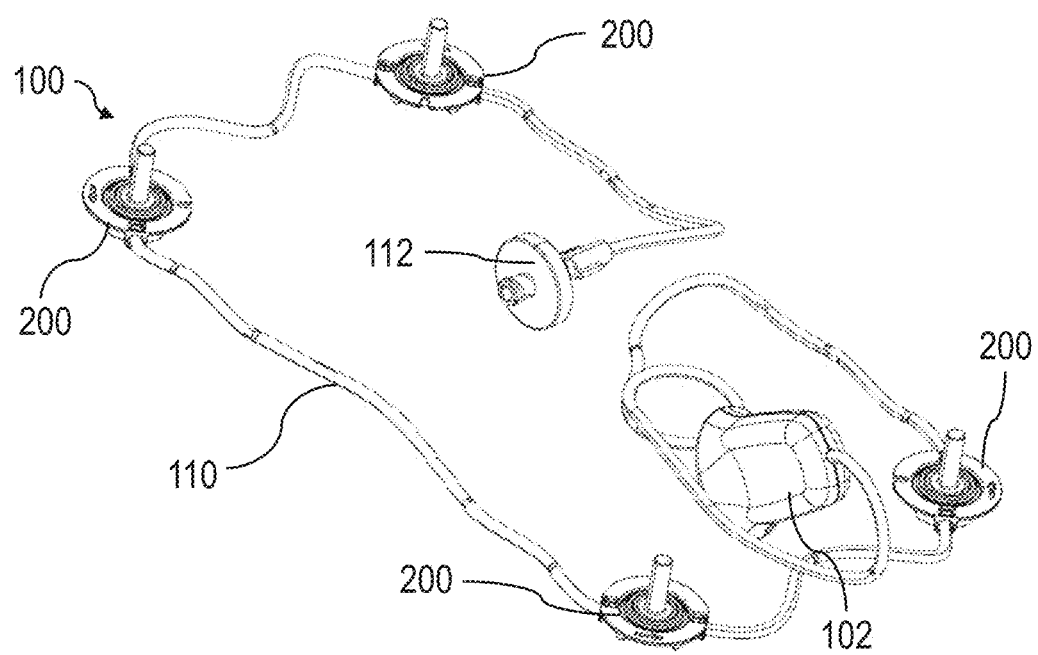
FIG. 3 is a perspective view of one embodiment of a first fluid distribution system.

FIG. 3 is a perspective view of one embodiment of a first fluid distribution system 100. The first fluid distribution system includes a first fluidic connector (not shown in the figure) of a fluidic interface 102, tubing 110, an air filter 112, and four spike assemblies 200. According to the embodiment shown in FIG. 3, the first fluidic connector may be configured to couple to any suitable patient device such as a syringe or infusion pump to withdraw fluid from the second fluid distribution system. In some embodiments, the fluidic connector may include a luer activated valve, single shut-off valve, double shut-off valve, dry break valve, bayonet mount coupler, or any other suitable valve that may prevent fluid from flowing out of the first fluidic connector prior to coupling with a patient device. In some embodiments, the air filter 112 is configured as a hydrophobic one-way filter configured to allow filtered air to pass into the first fluid distribution system while substantially preventing medicinal fluid from exiting. Accordingly, the air filter may allow medicinal fluid contained within a container to drain by gravity towards the fluidic interface without forming a negative pressure differential inside of the containers. The air filter may also allow passive drainage of the medicinal fluids without pumps or other energy-driven flow inducers. As discussed previously, each of the spike assemblies is configured to create fluidic communication between containers of medicinal fluids and the fluid distribution system. The tubing 110 interconnects each of the components in series, with the air filter disposed on one end of the tubing, and the fluidic interface disposed on an opposite end, and the spike assemblies arranged in between. Of course, any suitable order of fluid components of the fluid distribution line may be employed, as the present disclosure is not so limited. For example, one or more air filters and/or the fluidic interface 102 may be disposed between any of the spike assemblies 200.

In some embodiments, the fluid distribution system may be configured to pool and/or mix medicinal fluids. In the embodiment shown in FIG. 3, the first fluid distribution system 100 may be used to connect up to four separate containers of medicinal fluids. As each of the spike assemblies 200 is configured to flow to the next spike assembly, coupling multiple containers effectively pools (i.e., combines) the medicinal fluids for delivery via the fluidic interface 102 to any suitable patient device (e.g., syringe, infusion pump, etc.). In some embodiments, the spike assemblies may be configured to receive differing medicinal fluids which are mixed throughout tubing 110. In some embodiments, the number of spike assemblies, fluidic interfaces, and air filters may be chosen for pooling and/or mixing a predetermined volume of fluid. Furthermore, the number of spike assemblies, fluidic interfaces, air filters, and tubing may modify the flow rate of the medicinal fluid or mixed medicine supplied at the fluidic interface. Of course, the medicinal distribution system may be configured to pool and/or combine any number of medicinal fluids from any number of containers, as the present disclosure is not so limited. In some embodiments, the fluid distribution system may include a mixing chamber or other mixing features which are configured to further mix medicinal fluids.

Figure 4:
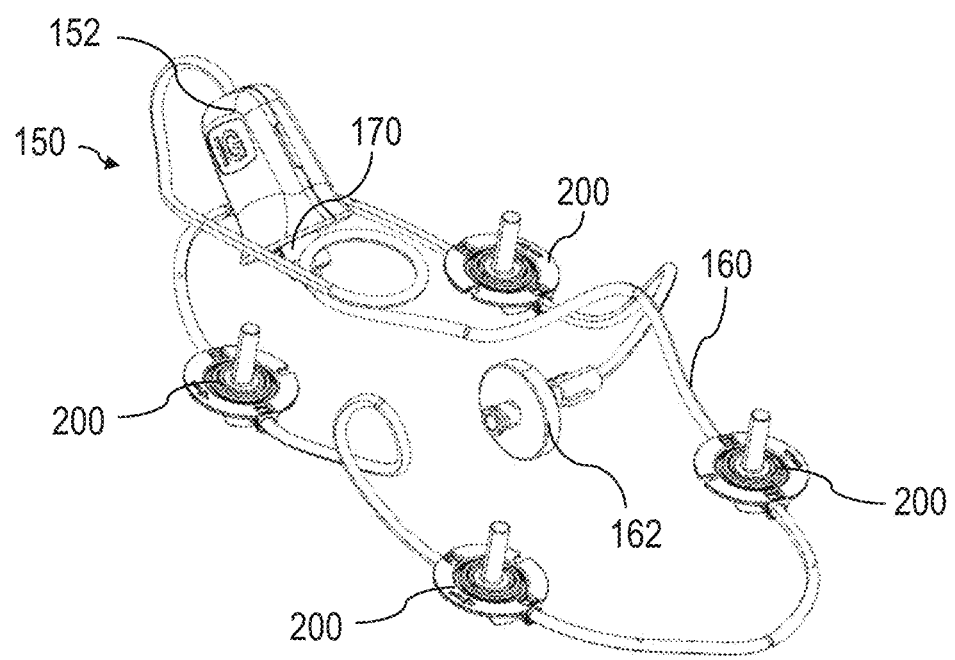
FIG. 4 is a perspective view of one embodiment of a second fluid distribution system.

FIG. 4 is a perspective view of one embodiment of a second fluid distribution system 150. Similar to the first fluid distribution system of FIG. 3, the second fluid distribution system includes a second fluidic connector 170 of a fluidic interface 152, a second air filter 162, and four spike assemblies 200. According to the embodiment shown in FIG. 4, the fluidic connector 170 is configured to be coupled to an infusion pump and includes a male adapter disposed at the end of the fluidic connector opposite the tubing. As discussed, previously, in some embodiments the fluidic connector 170 may include a luer activated valve or any other suitable valve which may prevent fluid flow prior to connection with the infusion pump. The second air filter 162 is configured to allow air into the fluid distribution system as medicinal fluids are withdrawn from the fluidic interface, replacing the lost volume of fluid with filtered air. The spike assemblies 200 may be configured to be individually connected to containers of medicinal fluids, so that the total volume of medicinal fluids may be pooled and supplied directly to the fluidic interface 152 rather than sourcing the medicinal fluids directly from the container until the total dosage volume is reached. That is, after the containers are connected to the fluid distribution system, the total dosage volume of fluid may be immediately delivered to a patient via the fluidic interface. The second fluidic interface may have any number of suitable modifications to modify aspects of the medicinal fluid delivery, including, but not limited to, changing the number of spike assemblies or air filters, changing the tubing size, changing the fluidic interface coupler, and adding mixing components.

In some cases where multiple medicinal fluids are administered to a patient in succession, there is a predetermined ratio of volume between medicinal fluids for a given dosage. Accordingly, medicinal fluids may be packaged together (e.g., in container units) so that the medicinal fluids may be administered in the proper ratio. In cases of successive fluid administration, a medicinal pooling device may include both a first fluid distribution system and a second distributions system corresponding to a first medicinal fluid and a second medicinal fluid, respectively. In some embodiments, the second fluid distribution system 150 may include an equal number of components (e.g., spike assemblies) contained in a first fluid distribution system (see FIG. 3). Such an arrangement may be beneficial where medicinal fluids are packaged in predetermined ratios in equal numbers of containers. In other embodiments, the first and second fluid distribution system may have differing numbers of components corresponding to typical numbers of containers used for dosage of separate medicinal fluids. Of course, the first and second fluid distribution system may have any suitable number of components for pooling and/or mixing medicinal fluids from multiple containers, as the present disclosure is not so limited.

Figure 5:
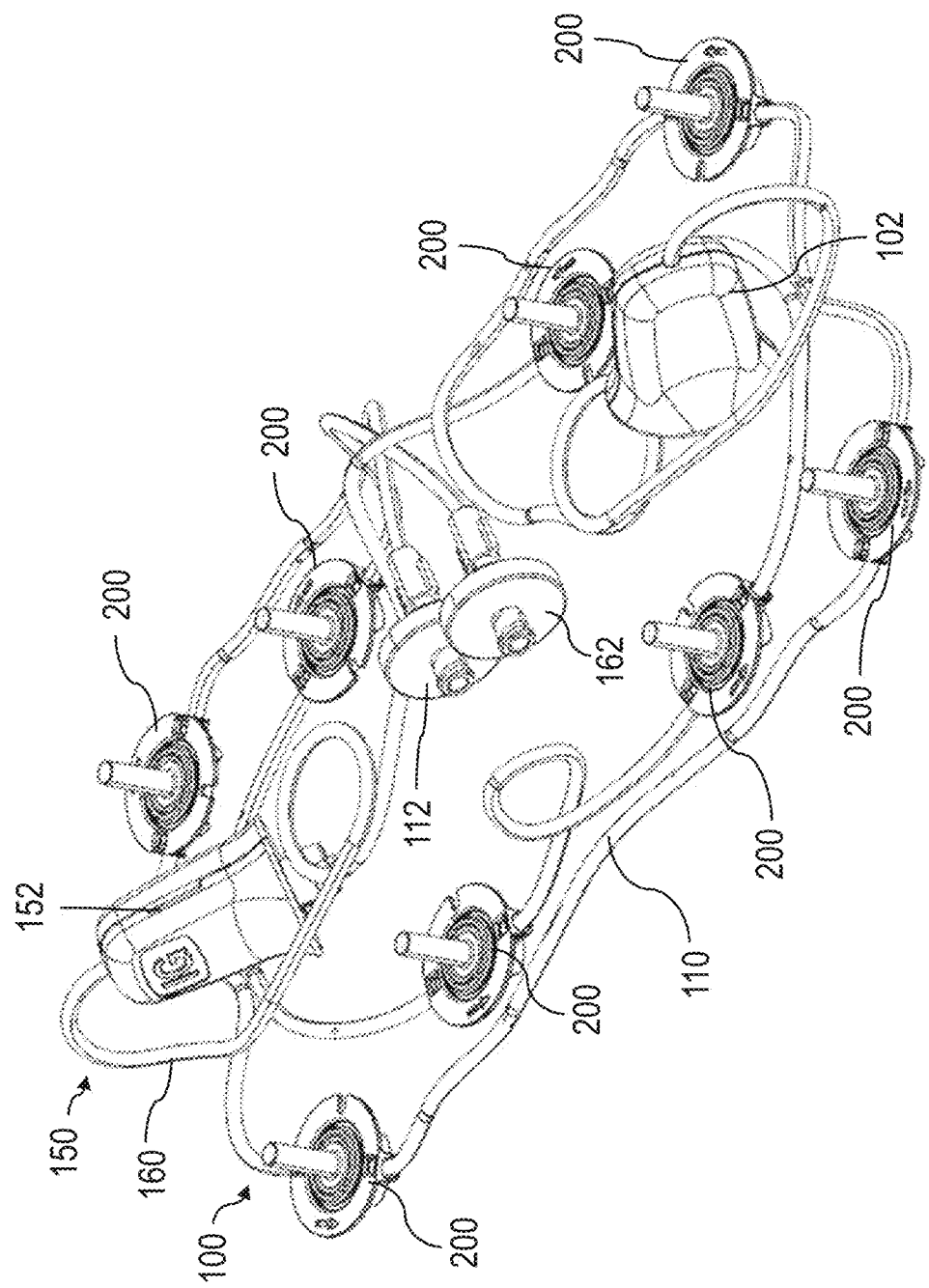
FIG. 5 is a perspective view of one embodiment of a combination of a first fluid distribution system and a second fluid distribution system for use in the medicinal pooling device of FIG. 1.

FIG. 5 depicts one embodiment of a combination of the first fluid distribution system 100 of FIG. 3 and the second fluid distribution system 150 of FIG. 4 configured for use in the medicinal pooling device of FIG. 1. As shown in FIG. 5, the first and second fluid distribution systems are not in fluidic communication with one another. Accordingly, the combination shown in FIG. 5 is suitable for administration of medicinal fluids separately to a patient via the first fluidic interface 102 and second fluidic interface 152. The first fluidic interface and second fluidic interface may be arranged so that the spike assemblies 200 in corresponding positions along the distribution systems are positioned in the same port of the medicinal pooling device (see FIG. 2). The combination of fluid distributions systems may be at least partially contained in a housing to protect and support the distribution systems, as shown in FIG. 2.

FIG. 6 depicts an exploded view of the first fluid distribution system 100 of FIG. 3. The fluid distribution system includes a female fluidic connector 120 which includes a luer activated valve disposed therein and is configured to be connected to a syringe so that the contents of the first fluid distribution system may be withdrawn by the syringe. The female fluidic connector may be disposed in a housing for ease of handling by a patient or medical professional (for example, see FIG. 3). In the embodiment of FIG. 6, the air filter 112 is coupled to the tubing 110 by a tubing coupler 114.

As shown in FIG. 6, the spike assemblies 200 each include a spike 202 and a spike sheath 220. The spike is configured to pierce a container of medicinal fluid, and includes an internal channel which fluidly connects the container to the first distribution system. The internal channel of the spike 202 may be a dual-lumen channel (i.e., two separate channels), with either side being connected to tubing 110. Accordingly, as fluid flows from the air filter toward the fluidic interface 102, the fluid will travel up one side of the spike 202 and down the other. In cases where air is disposed in the fluid distribution system 100, air will flow up one side of the spike to replace fluid volume that flows down the opposite side toward the fluidic interface. The spike sheath 220 is configured to create a seal around the spike, so that fluid cannot escape the fluid distribution system. In embodiments where the spike includes a dual-lumen internal channel, the spike sheath may fluidly connect the two lumens together, thereby permitting fluid flow towards the fluidic interface. The spike sheath may configured to be broken as a container of medicinal fluid is inserted onto and pierced by the spike, so that the medicinal fluid may be brought into fluidic communication with fluid distribution system without compromising the integrity of the fluid distribution system.

FIG. 7 depicts an exploded view of the second fluid distribution system 150 of FIG. 4. As discussed previously, the second fluid distribution system includes a fluidic interface 152 (housing not shown in the figure), an air filter 162, spike assemblies 200, and tubing 160. As shown in FIG. 7, the fluidic interface includes a male fluidic connector 170. The male fluidic connector includes a luer activated valve and is accessible to an infusion pump operated by a patient or medical professional. That is, the male fluidic connector may be used to withdraw pooled and/or mixed fluid from the second fluid distribution system to be infused into a patient during medicinal fluid administration. The male fluidic connector may be disposed in a housing (for example, see FIG. 4) for ease of handling. The air filter 162 is connected to the tubing 160 via tubing coupler 164. Similar to the first fluid distributions system of FIG. 6, the spike assemblies 200 include a spike 202 and a spike sheath 220, where the spike may include a dual-lumen internal channel which is fluidly coupled by the spike sheath.

Figure 8A:
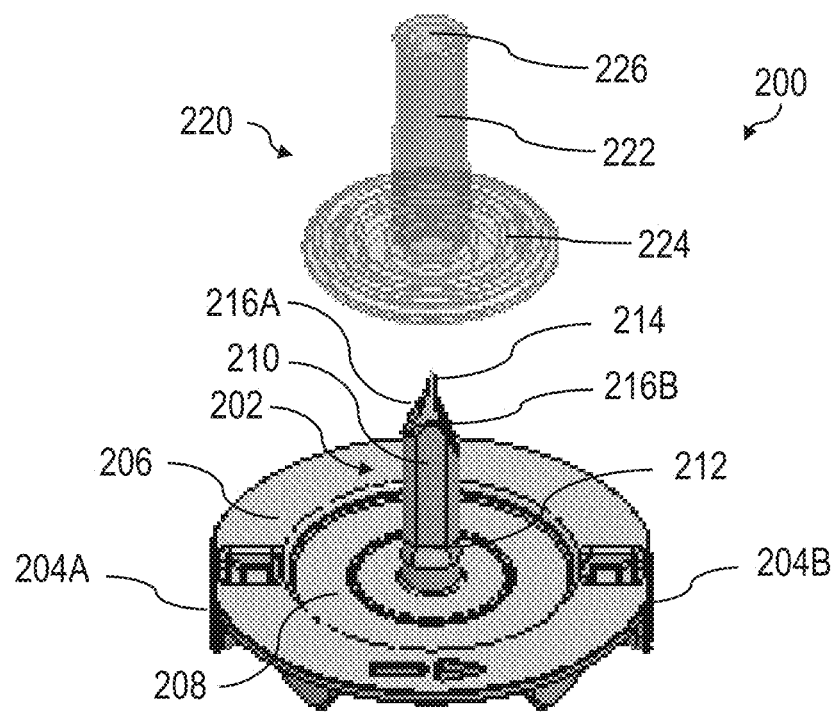
FIG. 8A is an exploded view of one embodiment of a spike and spike sheath.

FIG. 8A depicts an exploded view of one embodiment of a spike assembly 200 including a spike 202 and a spike sheath 220. As shown in FIG. 8A, the spike 202 includes an inlet 204A, an outlet 204B, a base 206, a first body portion 210 and a second body portion 212. Together, the first body portion and the second body portion form the shaft of the spike. A dual-lumen internal channel extends through the shaft of the spike, terminating in inlet opening 216A and outlet opening 216B which are fluidly connected to the inlet 204A and outlet 204B, respectively. In some embodiments, as shown in FIG. 8A, the inlet opening 216A may be positioned vertically higher than outlet opening 216B, which may facilitate the introduction of air into any container volume fluidly connected to the spike as a medicinal fluid flows out through the outlet opening. A spike tip 214 is disposed on the first body portion, and is configured to pierce the spike sheath 204 as well as a container pushed onto the spike.

As shown in FIG. 8A, the spike sheath 220 includes a sheath shaft 222, a sheath base 224, and a sheath tip 226. The sheath base 224 is configured to support the sheath shaft 222 and fits into recess 208 formed in the base 206 of the spike 202. The sheath shaft 222 defines an internal volume, and is configured to fit around the spike shaft formed by first body portion 210 and second body portion 212. According to the embodiment shown in FIG. 8A, when the spike is received by the spike sheath, the shaft and base create a seal around the second body portion 212. In particular, a sealing ring (for example, see FIG. 10) may be molded on the internal diameter of the sheath shaft 222 configured to create a seal with second body portion 212 of the spike 202. The second body portion may have a circular cross section which promotes a uniform sealing force applied across the entire circumference of the internal sealing rings to inhibit leaking of fluid. In some embodiments, multiple sealing rings (e.g., two or more sealing rings), may be used to provide redundancy to the seal between the spike sheath and the spike. In other embodiments, the spike sheath may create a fluid seal with the first body portion, base or any other suitable component of the spike 202. The sheath tip 226 fluidly connects the inlet opening 216A and the outlet opening 216B so that fluid may flow from the inlet to the outlet when a container has not been inserted onto the spike assembly 200.

The inventors have recognized that, in some cases, it may be desirable to reduce the number of components handled by a patient or medical professional during a medicinal fluid administration process. Additional touching and handling of sterile components may compromise their sterility or otherwise negatively affect treatment of the patient. Accordingly, in some embodiments, the spike sheath may be configured to be broken by a container inserted onto the spike assembly 200 so that a patient or medical professional may not have to handle any component of the spike assembly. In some embodiments, the spike sheath 220 may be formed of a material that is able to be pierced by the spike tip 214 and is also compressible. For example, the spike sheath may be formed of a thin plastic that may provide a fluid seal for the spike but is easily breakable and compressible. According to this embodiment, as a container is pressed onto the spike assembly, the container may force the sheath shaft 222 and sheath tip 226 towards the spike base 206. The sheath shaft 222 may abut the recess 208 formed in the spike base and resist this motion, resulting in the sheath shaft 222 compressing (e.g., folding/crumpling, and in some cases, folding/crumpling in an accordion-like manner) towards the base. As the sheath tip contacts the spike tip 214, it may be pierced and broken so that the tip does not resist further compression of the sheath shaft towards the base. During this process, the sheath base and the sheath shaft may maintain a fluid seal around the second body portion 212 of the spike so that no fluid is lost when the spike creates fluidic communication with the container of medicinal fluid (e.g., by piercing a seal or stopper of the container). In some embodiments, the inserted container may form a fluid seal around the spike 202 instead of the sheath as the sheath is broken to prevent fluid loss.

Figure 8B:
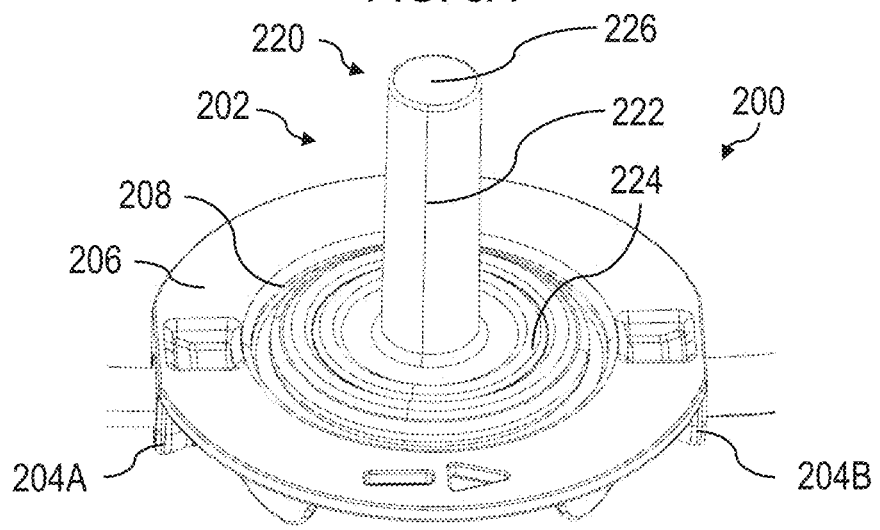
FIG. 8B is a perspective view of the spike and spike sheath of FIG. 8A, in assembled form.

FIG. 8B depicts the spike 202 and spike sheath 220 of FIG. 8A fully assembled, with the sheath placed over and receiving the first body portion and the second body portion (see FIG. 8A). As clearly shown in FIG. 8B, the sheath base 224 is received in the recess 208 formed in the base 206 of the spike. Accordingly, the sheath is secured to the spike, and the sheath base may resist lateral or longitudinal (i.e., in the direction toward the base) movement of the sheath. The sheath base may resist forces applied to the sheath tip 226 and/or sheath shaft 222, so that the sheath tip and/or sheath shaft compress down towards the base. In some embodiments, as the sheath tip and sheath shaft crumple towards the base, the sheath base may maintain a fluidic seal around the spike so that no medicinal fluid is lost during the process.

Figure 9A:
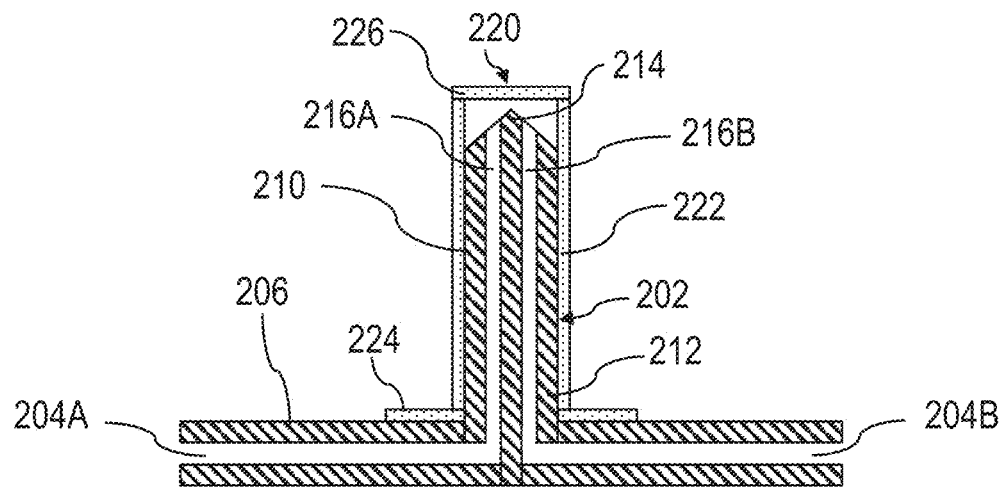
FIG. 9A is a schematic of another embodiment of a spike and spike sheath.

FIG. 9A depicts a cross-sectional schematic of another embodiment of a spike 202 and spike sheath 220. As discussed previously, the spike includes an inlet 204A fluidly connected to an inlet opening 216A and an outlet 204B fluidly connected to an outlet opening 216B. The dual-lumen internal channel formed by the inlet and the outlet extend the length of the spike shaft formed by a first body portion 210 and a second body portion 212. The inlet and the outlet are separate from one another, and terminate in the inlet opening and outlet opening disposed adjacent the spike tip 214. The first body portion and second body portion extend out from a base 206, which supports the spike and forms at least part of the inlet and the outlet.

As shown in FIG. 9A, the spike sheath 220 is fit over the spike 202, so that the first body portion 210, second body portion 212, and spike tip 214 are substantially enclosed by the spike sheath. In some embodiments, the spike sheath serves as a protective barrier for the spike, which may be sterile for use in opening a container of a medicinal fluid. Accordingly, the sheath may maintain the sterility of the spike until the moment the spike is used to open the container. In the embodiment of FIG. 9A, the spike sheath is in an uncompressed position and is configured to create a seal around the second body portion of the spike, so that any fluid that exits the inlet opening 216A or outlet opening 216B is not able to escape the spike sheath. Accordingly, the spike sheath fluidly couples the inlet opening to the outlet opening, and serves as a conduit for fluid to pass between the two. For example, fluid flowing into the inlet 204A and out of the inlet opening may be conducted into the outlet opening by the spike sheath and flow out of the outlet 204B.

In some embodiments of a medicinal pooling device where multiple spikes may be employed, the spike sheaths may provide selectivity in the number of containers of medicinal fluid used with the medicinal pooling device. For example, in a medicinal pooling device with four spikes arranged along a fluid distribution system, a container of a medicinal fluid may be inserted onto one spike to fluidly connect the internal volume of the container to the fluid distribution system. In this example, the fluid may be transmitted from the container throughout the fluid distribution system including through the three remaining spikes. The spike sheaths on each of the three remaining spikes cause the spikes to function as a normal conduit, and the fluid is not impeded if some of the spikes are not used during an administration process. In some embodiments, the spike sheaths may obviate the need for complex valves or other devices which may regulate fluid flow, thereby simplifying the fluid distribution system. In other embodiments, however, the spike and/or fluid distribution system may also include check valves, adjustable valves, or any other suitable devices for regulating fluid flow.

According to the embodiment shown in FIG. 9A, the spike sheath 220 includes a sheath shaft 222, a sheath base 224, and a sheath tip 226. The sheath base may support the sheath shaft 222, which extends from the base and forms an internal volume configured to receive the spike 202. The sheath base and the sheath shaft create the fluidic seal around the spike shaft formed by the first body portion 210 and the second body portion 212. The sheath tip serves to cap the internal volume formed by the sheath shaft, so that the spike sheath creates a fluidly sealed volume around the spike suitable to conduct fluid between the inlet and the outlet when the sheath is in an uncompressed position. The sheath shaft and the sheath tip may be formed of a thin material that is compressible in a longitudinal direction towards the spike base 206. The sheath base 224 may serve to resist force in the longitudinal direction, so that force applied to the sheath tip 226 compresses the sheath shaft and/or sheath tip towards the base. The sheath tip may be configured to be pierced by the spike tip 214 when the spike sheath is compressed toward the spike base.

In some cases, the spike 202 and/or the spike sheath 220 may exert frictional resistance when the spike is used to pierce a container. Accordingly, in some embodiments, the spike 202 may include a lubricant disposed on the spike tip 214, first body portion 210, and/or the second body portion 212 configured to reduce the frictional resistance. According to the embodiments shown in FIG. 9A, the lubricant may be disposed directly on the spike and covered by the spike sheath. Of course, the lubricant may be disposed on an exterior of the spike sheath or any other portion of the spike or spike sheath as the present disclosure is not so limited. The lubricant may be any suitable lubricant for lowering frictional resistance between the spike, spike sheath, and/or container when the spike is used to pierce the container, including, but not limited to, silicone lubricants (e.g., DOW CORNING 360), perfluoropolyether (PFPE) lubricants (e.g., NYEMED 7471), synthetic hydrocarbon lubricants, esters, and polyglycols.

Figure 9B:
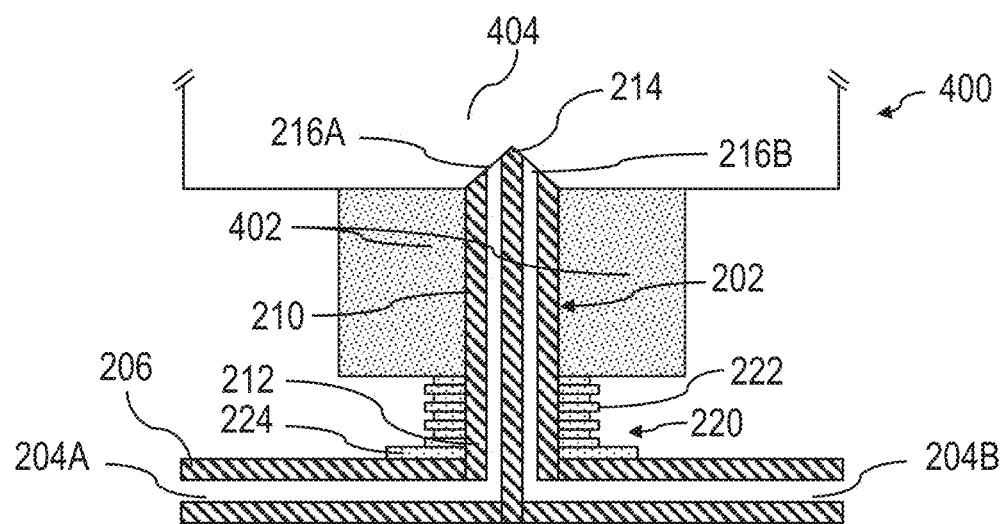
FIG. 9B is a schematic of the spike and spike sheath of FIG. 9A after a container has been inserted onto the spike.

FIG. 9B shows the spike 202 and spike sheath 220 of FIG. 9A after a container 400 has been inserted onto the spike. The container includes a stopper 402 and an internal volume 404 in which a medicinal fluid may be disposed. The stopper 402 may be composed of a material that is able to be pierced by the spike 202 so that the inlet 204A and the outlet 204B may be brought into fluidic communication with the internal volume 404. For example, the stopper may be made of a rubber material such as polyurethane, neoprene, latex, silicone, EPDM, FKM, or any other suitable material. As the container is pushed onto the spike 202, the stopper 402 contacts the spike sheath 220 first and applies force to the spike sheath in a longitudinal direction towards the spike base 206. As force is applied to the spike sheath, the sheath shaft 222 compresses towards the spike base, and the sheath tip 226 is brought into contact with the spike tip 214. After a predetermined amount of displacement of the spike sheath, the spike tip pierces the spike sheath and begins to pierce the stopper 402. As the container is pushed fully onto the spike so that the spike fully pierces the container, the spike sheath is kept in contact with the stopper and is compressed down towards the spike base. As shown in FIG. 9B, the sheath shaft and broken sheath tip may be folded many times upon itself (e.g., in an accordion-like manner) to occupy less vertical space. During this compression process, the sheath base 224 resists the force applied by the container, allowing the sheath shaft to compress. As shown in FIG. 9B, the spike sheath is in a compressed position and the internal volume 404 is in fluid communication with the inlet 204A and the outlet 204B.

According to the embodiment shown in FIG. 9B, the stopper 402 creates a fluidic seal around the spike 202 once the spike pierces the stopper. As shown in FIG. 9B, the sheath shaft 222 is pierced through by the spike tip 214 and compressed around the first body portion 210 of the spike shaft by the stopper 402 so that the sheath no longer forms a seal against the spike shaft. The stopper 402 creates a fluid seal around the spike 202. The stopper may be composed of any suitable material for creating the fluidic seal against the spike, as the present disclosure is not so limited.

In the embodiment depicted in FIG. 9B, once the internal volume 404 of the container 400 is brought into fluidic communication with the inlet opening 216A and the outlet opening 216B, the medicinal fluid contained in the internal volume may flow and fill the fluid distribution system. The inlet 204A may be connected to tubing in the direction of an air filter (for example, see FIG. 6-7) that filters air and allows air to enter the fluid distribution system. The outlet 204B may be connected to tubing in the direction of a fluidic interface (for example, see FIG. 6-7) which may be used to withdraw and administer the medicinal fluid from the internal volume. According to the embodiment of FIG. 9B, the internal volume of the container may be positioned above the components of the fluid distribution system. Accordingly, any fluid disposed therein may be driven by gravity to fill the fluid distribution system and flow toward the fluidic interface. Air may be introduced into the internal volume via the air filter and inlet 204A to replace the volume of fluid that flows out of the outlet 204B or otherwise leaves the internal volume of the container.

Figure 10:
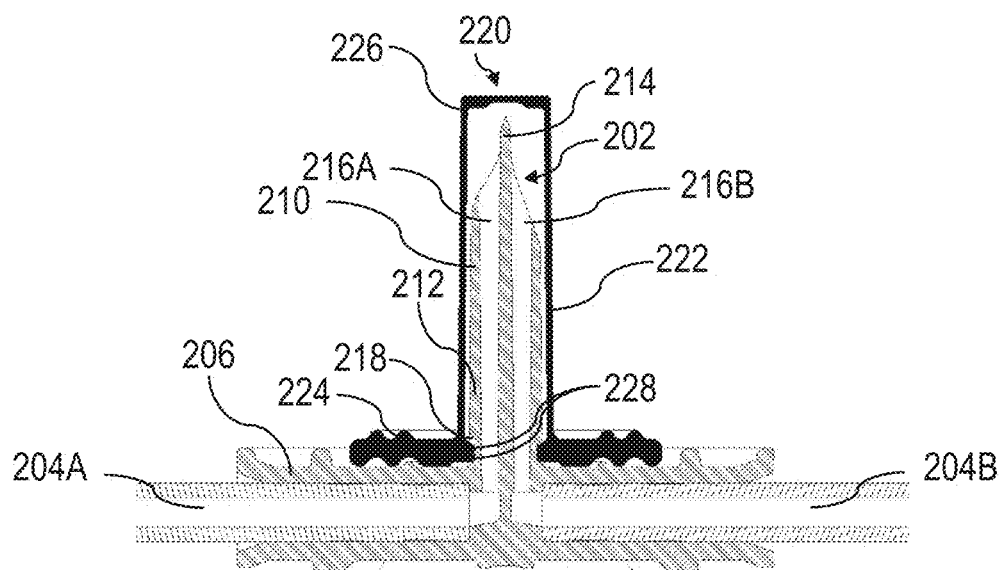
FIG. 10 is a cross sectional view of another embodiment of a spike and a spike sheath.

FIG. 10 depicts a cross-sectional view of another embodiment of a spike 202 and spike sheath 220. Similar to the embodiment of FIG. 9A, the spike includes an inlet 204A fluidly connected to an inlet opening 216A and an outlet 204B fluidly connected to an outlet opening 216B. The dual-lumen internal channel formed by the inlet and the outlet extend the length of the spike shaft formed by a first body portion 210 and a second body portion 212 and are separate from one another. The inlet and outlet terminate in the inlet opening and outlet opening disposed adjacent the spike tip 214, respectively. The first body portion and second body portion extend out from a base 206, which supports the spike and forms at least part of the inlet and the outlet.

As shown in FIG. 10, the spike sheath 220 is fit over the spike 202, so that the first body portion 210, second body portion 212, and spike tip 214 are substantially enclosed by the spike sheath. According to the embodiment of FIG. 10, the spike sheath serves as a protective barrier for the spike, which may be sterile for use in opening a container of a medicinal fluid. Accordingly, the sheath may maintain the sterility of the spike until the moment the spike is used to open the container. As shown in FIG. 10, the spike sheath is in an uncompressed position and is configured to create a seal around the second body portion of the spike, so that any fluid that exits the inlet opening 216A or outlet opening 216B is not able to escape the spike sheath. Accordingly, the spike sheath fluidly couples the inlet opening 216A to the outlet opening 216B, and serves as a conduit for fluid to pass between the two. For example, fluid flowing into the inlet 204A and out of the inlet opening 216A may be conducted into the outlet opening 216B by the spike sheath and flow out of the outlet 204B.

According to the embodiment of FIG. 10, the spike sheath 220 includes multiple sealing rings 228 disposed inside of the sheath shaft 222. The sealing rings extend radially inward from the sheath shaft to engage the second body portion 212 of the spike. The sealing rings may be formed with the spike sheath, or may be separately formed (e.g., as an O-ring) and subsequently positioned in the spike sheath. According to the embodiment shown in FIG. 10, the sealing rings and second body portion are circular, so that the sealing rings evenly engage the spike across the entire circumference of the spike. That is, the circular shape promotes even tension throughout the entire circumference of the sealing rings to create an evenly pressured seal. Without wishing to be bound by theory, sealing around an elliptically shaped second body portion may create variations in sealing pressure along the circumference of the spike which may result in a less secure fluidic seal. According to the embodiment of FIG. 10, the second body portion of the spike includes a ledge 218 into which the sealing rings may seat to promote a seal and secure the spike sheath to the spike. Of course, the second body portion may have any suitable shape, as the present disclosure is not so limited. According to the embodiment shown in FIG. 10, the spike sheath includes two sealing rings. Without wishing to be bound by theory, a single sealing ring may be suitable to inhibit fluid from escaping from the spike sheath. In cases where a single sealing ring is compromised (e.g., by manufacturing, mishandling, etc.) the second sealing ring may maintain the fluidic seal between the spike and the spike sheath. Of course, any suitable number of sealing rings may be employed, as the present disclosure is not so limited.

Figure 11:
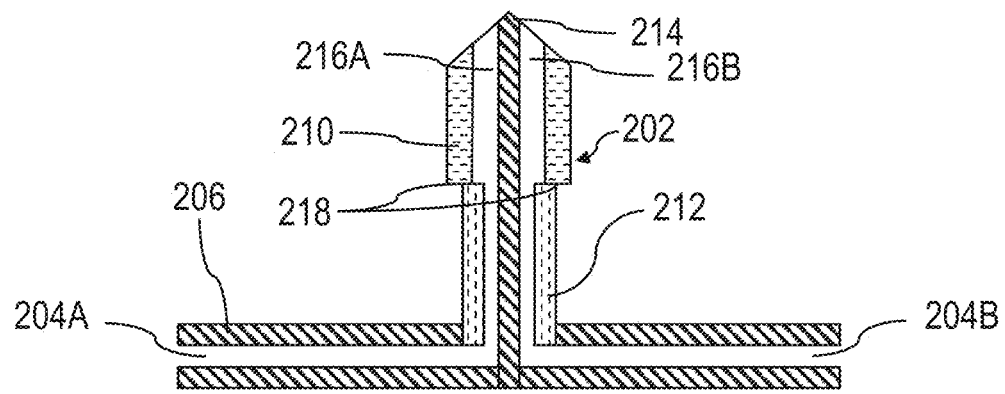
FIG. 11 is a schematic of yet another embodiment of a spike.

FIG. 11 shows a schematic of yet another embodiment of a spike 202 with a differently shaped first body portion 210 and second body portion 212. In some cases, differently dimensioned and/or shaped body portions of the spike may affect fluidic sealing performance between a spike and a spike sheath and/or stopper of a container. That is, the spike sheath and/or stopper of the container may have a shape complementary to that of at least one of the first body portion and the second body portion, so that an adequate fluidic seal may be created around the spike so that fluid is substantially prevented from escaping around the spike. According to the embodiment shown in FIG. 11, the first body portion 210 has an elliptical cross section, having a major axis diameter larger than the diameter of the circular cross section of the second body portion 212. That is, the major axis of the first body portion 210 has a diameter which is larger than the major axis of the second body portion 212. The first body portion 210 transitions abruptly to the radius of the second body portion creating a ledge 218. As shown in FIG. 11, the ledge 218 may function as a barb that serves to connect a spike sheath or container stopper. Alternatively or in addition, the ledge 218 may function as a seat for a sealing ring of the spike sheath. In some embodiments, such an arrangement may provide additional radial space around the second body portion in which a sheath shaft may compress which may reduce the force used to break and compress the sheath.

In some embodiments, a first body portion and a second body portion may compose any suitable portion of a spike. For example, the first body portion may form the majority of a spike shaft, while the second body portion is a small projection disposed on the first body portion. As another example, the first body portion and second body portion may transition seamlessly between the each other, so that the first body portion and second body portion are a single component. In some embodiments, the first and second body portions may have different shapes and/or dimensions. In other embodiments, the first and second body portions may have the same shape and/or dimensions. Thus, the first and second body portions may take any suitable form and may form any two regions of the spike shaft.

Figure 12:
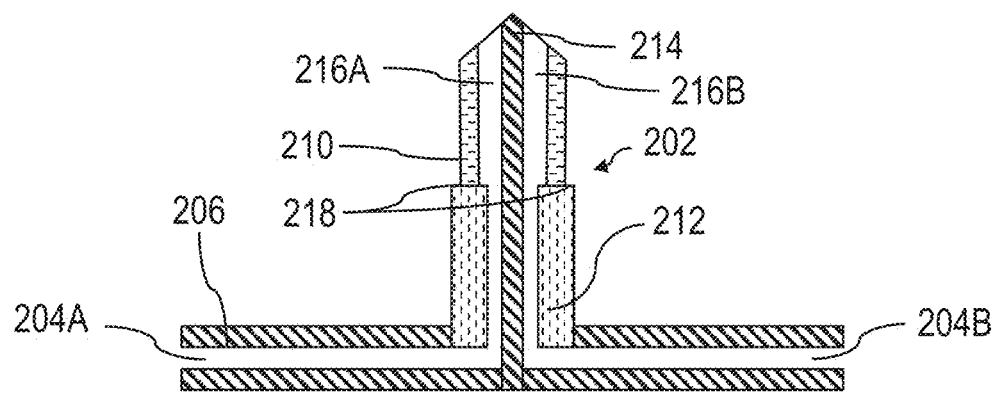
FIG. 12 is a schematic of yet another embodiment of a spike.

FIG. 12 is a schematic of yet another embodiment of a spike 202 including a first body portion 210 that has different dimensions from a second body portion 212. Similar to the embodiment of FIG. 11, the first body portion has an elliptical cross section. However, in the embodiment shown in FIG. 11 the width of the first body portion shown corresponds to a minor axis of the elliptical cross section. Additionally, the second body portion 212 has a circular cross section. In this embodiment, the major axis of the second body portion is radially larger (i.e., has a larger diameter) than the minor axis of the first body portion 210. The first body portion transitions abruptly to the second body portion, forming ledge 218. Such an arrangement may promote sealing with a spike sheath and/or a stopper of a container. For example, a stopper pushed onto the spike 202 may abut the ledge 218, and any hole of imperfections in the stopper created by the first body portion may be sealed by the second body portion. As another example, a spike sheath disposed around the spike may stretch around the second body portion when compressed, increasing contact and improving the seal provided by the spike sheath. In some embodiments, the ledge 218 may be inclined to provide a less abrupt transition between the first body portion and the second body portion.

Figure 13:
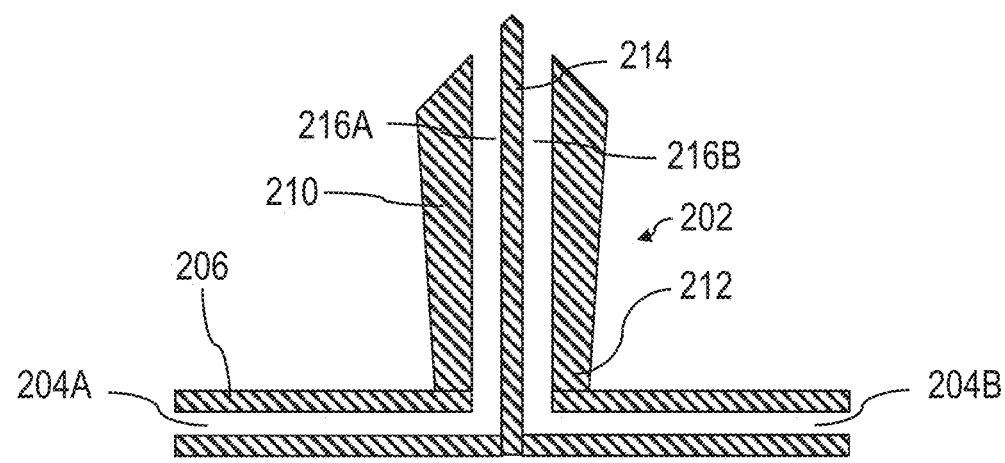
FIG. 13 is a schematic of yet another embodiment of a spike.

FIG. 13 is a schematic of yet another embodiment of a spike 202 including a first body portion 210 having different dimensions than a second body portion 212. As shown in FIG. 13, the first body portion has an elliptical cross sectional shape with a major axis corresponding to the width shown while the second body portion has a circular cross sectional shape. As shown in FIG. 13, the major axis of the first body portion is radially larger (i.e., has a larger diameter) than the major axis of the second body portion. The first body portion transitions seamlessly to the second body portion, so that no ledge or other discontinuity is formed in the spike shaft. Such an arrangement may promote a consistent insertion of a container onto the spike, as no discontinuities may catch or otherwise more greatly resist force applied to the container to insert it onto the spike. The differently dimensioned first body portions and second body portions may provide sealing for a container stopper or spike sheath, even with a lack of abrupt transitions or discontinuities.

Figure 14:
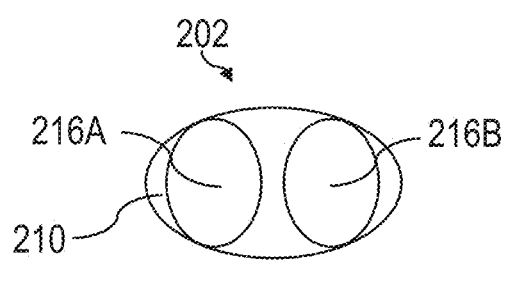
FIG. 14 is a schematic of one embodiment of a cross section for a first body portion of a spike.

FIG. 14 shows one embodiment of a transverse cross section of a first body portion 210 of a spike 202. The first body portion 210 includes an inlet opening 216A and an outlet opening 216B formed therein. As shown in FIG. 14, the first body portion has an elliptic cylinder shape with an elliptical transverse cross-section. Without wishing to be bound by theory, an elliptic cylinder shape may reduce the total surface area of the spike 202 without compromising the inlet or outlet openings, which may reduce the force required to pierce a container and/or spike sheath with the spike. In the embodiment of FIG. 14, the inlet opening and the outlet opening may be sized to form the sides of the first body portion, so that a small amount of extra area is occupied by the first body portion. As shown in FIG. 14, the inlet opening and outlet opening form a portion of the long sides of the elliptic cylinder first body portion.

Figure 15:
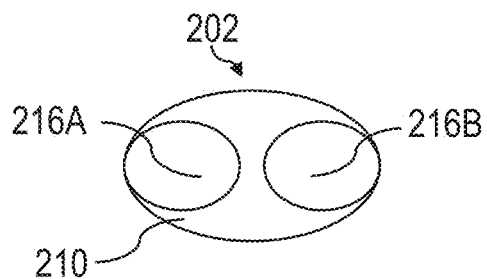
FIG. 15 is a schematic of another embodiment of a cross section for a first body portion of a spike.

FIG. 15 shows another embodiment of a transverse cross section of a first body portion 210 of a spike 202. Similar to the embodiment of FIG. 14, the first body portion includes an inlet opening 216A and an outlet opening 216B. The first body portion has an elliptic cylinder shape with an elliptical transverse cross section. Compared to the embodiment of the FIG. 14, the inlet opening and outlet opening are oriented to form a portion of the short sides of the elliptic cylinder. Such arrangement may provide additional structural support for a spike tip aligned with the center of the first body portion.

Figure 16:
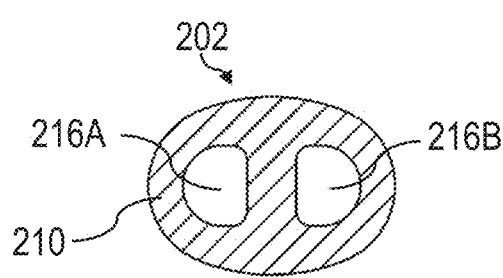
FIG. 16 is a schematic of yet another embodiment of a cross section for a first body portion of a spike.

FIG. 16 shows yet another embodiment of a transverse cross section of a first body portion 210 of a spike 202. Similar to the embodiment of FIGS. 14-15, the first body portion includes an inlet opening 216A and an outlet opening 216B. The first body portion has an elliptic cylinder shape with an elliptical transverse cross section. Compared to the embodiment of the FIGS. 14-15, the inlet opening and outlet opening each have a "D" shape, with the inlet opening and outlet opening opposing one another (i.e., the flat portions of the "D" are facing each other). Such an arrangement may offer additional structural support for a spike tip aligned with the center of the first body portion. Additionally, the D-shaped lumens allow a consistent wall thickness to be maintained throughout the first body portion while maintaining suitable cross sectional area of the lumens. Of course, the first body portion 210, inlet opening 216A, and outlet opening 216B may employ any suitable structure and arrangement, as the present disclosure is not so limited.

Figure 17:
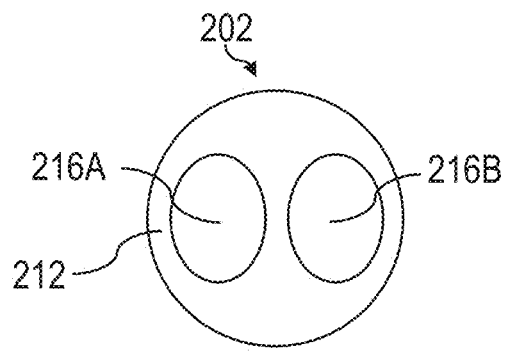
FIG. 17 is a schematic of one embodiment of a cross section for a second body portion of a spike.

FIG. 17 shows one embodiment of a transverse cross section of a second body portion 212 of a spike 202. The second body portion has a cylindrical shape with a circular transverse cross section, including an inlet opening 216A and an outlet opening 216B disposed therein. Compared with the first body portions 210 shown in FIGS. 14-16, the second body portion 212 of the embodiment of FIG. 17 has a different shape with more area occupied by the second body portion. Without wishing to be bound by theory, the shape of the second body portion may affect the quality of a fluid seal formed between the second body portion and a spike sheath and/or container stopper. In some embodiments, a circular cross-sectional shape may provide a consistent and reliable fluidic seal by promoting even sealing pressure around the entire circumference of the second body portion. Accordingly, in some embodiments, a first body portion and a second body portion may have different shapes and/or size to better perform different functions of the spike 202. For example, a first body portion may be formed according to the embodiment shown in FIG. 14 to ease piercing of a spike sheath and/or container stopper while a second body portion may be formed according to the embodiment shown in FIG. 17 to promote fluidic sealing between the spike and the spike sheath and/or container stopper. Of course, any suitable shapes for the first body portion and the second body portion may be employed, as the present disclosure is not so limited.

Figure 18:
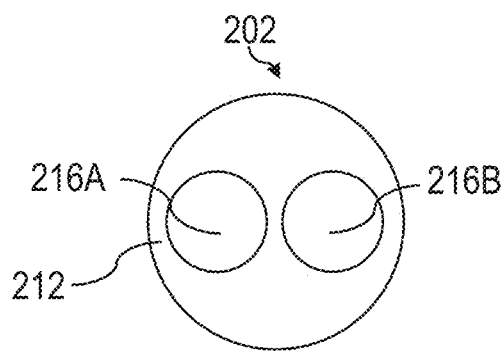
FIG. 18 is a schematic of another embodiment of a cross section for a second body portion of a spike.
Figure 19:
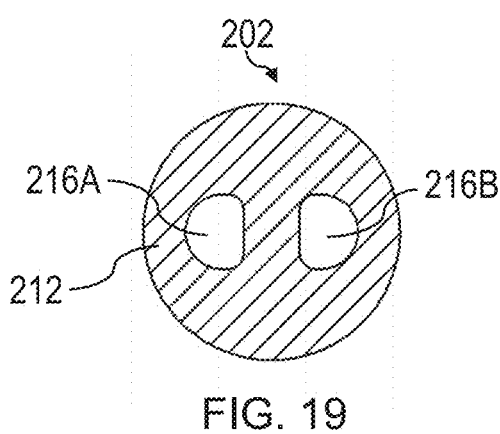
FIG. 19 is a schematic of another embodiment of a cross section for a second body portion of a spike.

FIGS. 18-19 show other embodiments of a transverse cross section of a second body portion 212 of a spike 202. Similar to the embodiment shown in FIG. 17, the second body portions shown in FIGS. 18-19 have a cylindrical shape with a circular transverse cross section and include an inlet opening 216A and an outlet opening 216B disposed therein. According to the embodiment shown in FIG. 18, the inlet opening and the outlet openings are formed in a circular shape with less area occupied than the elliptical openings of FIG. 17. Accordingly, the shape and/or size of the inlet opening or outlet opening may change between first and second body portions or within one of the first body portion and the second body portion. Alternatively, as shown in FIG. 19, the inlet opening 216A and outlet opening 216B each have a "D" shape with the inlet opening "D" opposing the outlet opening "D". Of course, the inlet opening and outlet opening may have any suitable shape in the second body portion, as the present disclosure is not so limited.

Figure 20A:
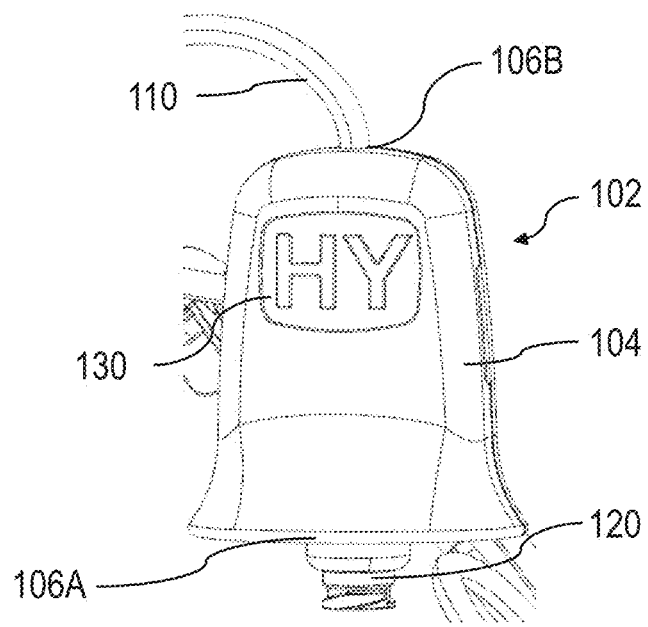
FIG. 20A is a perspective view of one embodiment of a fluidic interface.

FIG. 20A shows one embodiment of a fluidic interface 102 disposed at the end of a fluid distribution system. The fluidic interface includes a housing 104 which includes a first aperture 106A and a second aperture 106B. The housing 104 holds a female fluidic connector 120 which protrudes out of the first aperture 106A. The female fluidic connector is configured to connect to a syringe for withdrawing fluid from a medicinal pooling device. The female fluidic connector is connected to tubing 110 which enters the housing through second aperture 106B. The housing 104 is significantly larger than the female fluidic connector, making the fluidic interface easier to handle and manipulate for a patient or medical professional using the fluidic interface.

As shown in FIG. 20A, the fluidic interface may include an indicator 130. The indicator is configured to indicate information relating to a medicinal fluid supplied at the fluidic interface, instructions relating to an administration process, or other useful information pertinent to a patient or medical professional. In some embodiments, the indicator may be a visual indicator, a tactile indicator (e.g., bump dots in Braille), or a combination of the two. In the embodiment of FIG. 20A, the indicator is configured as text. Alternatively or in addition, the indicator may be a distinct color or any other non-text marking that conveys information to a patient or medical professional. Of course, any suitable combination of indicators may be used, including, but not limited to, text markings, non-text markings, symbols, bump dots, and colors.

Figure 20B:
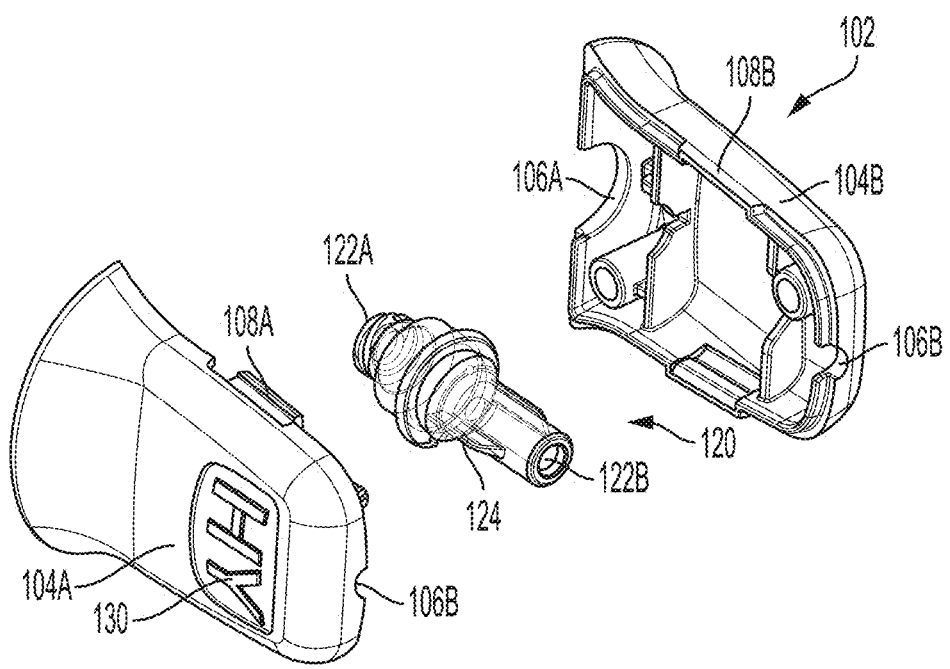
FIG. 20B is an exploded view of the fluidic interface of FIG. 20A.

FIG. 20B is an exploded view of the fluidic interface 102 of FIG. 20A. As shown in FIG. 20B, the fluidic interface includes a housing split into a first portion 104A and a second portion 104B as well as a female fluidic connector 120 disposed at least partially inside of the housing. As discussed previously, the housing 104 includes a first aperture 106A and a second aperture 106B which allows access to the internal volume defined by the housing. The first portion 104A of the housing also includes at least one latch 108A and the second portion 104B of the housing includes at least one latch receptacle 108B configured to receive the latch. The latch and latch receptacle may be used to secure the first and second halves of the housing together to enclose and secure the female fluidic connector 120.

As shown in FIG. 20B, the female fluidic connector 120 includes a first end 122A and a second end 122B. The first end is configured to mate with another suitable fluidic connector to a syringe or another patient device (e.g., an infusion pump). The female fluidic connector 120 may include a luer activated valve or any other suitable valve that may promote sterility or inhibit the flow of medicinal fluid prior to connection to the syringe. The first end 122A is arranged to be disposed in and project out from the first aperture 106A of the housing. The second end 122B is arranged to be fully enclosed in the housing and recessed back from the second aperture 106B. Accordingly, tubing may be inserted through the second aperture to fluidly connect the female fluidic connector to a fluid distribution system. As shown in FIG. 20B, the female fluidic connector also includes alignment features 124 that may secure the female fluidic connector inside of the housing when the first portion 104A and second portion 104B are combined to prevent significant relative movement between the housing and the female fluidic connector.

Figure 21A:
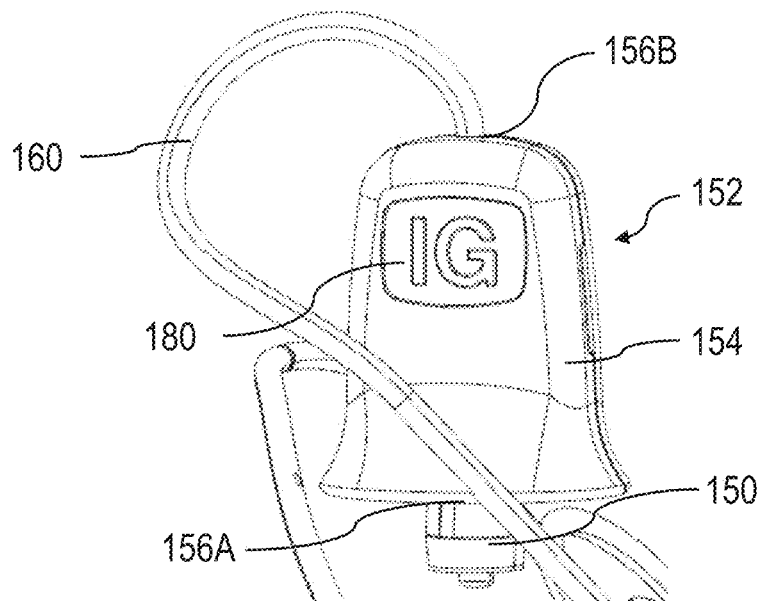
FIG. 21A is a perspective view of another embodiment of a fluidic interface.

FIG. 21A shows another embodiment of a fluidic interface 152 disposed at the end of a fluid distribution system. Similar to the embodiment of FIG. 20A, the fluidic interface includes a housing 154 including a first aperture 156A and a second aperture 156B. A male fluidic connector 170 is disposed in and projects out from the first aperture, and tubing 160 is disposed and extends from the second aperture 156B. An indicator 180 is disposed on the housing to convey information to a patient or medical professional using the fluidic interface.

Figure 21B:
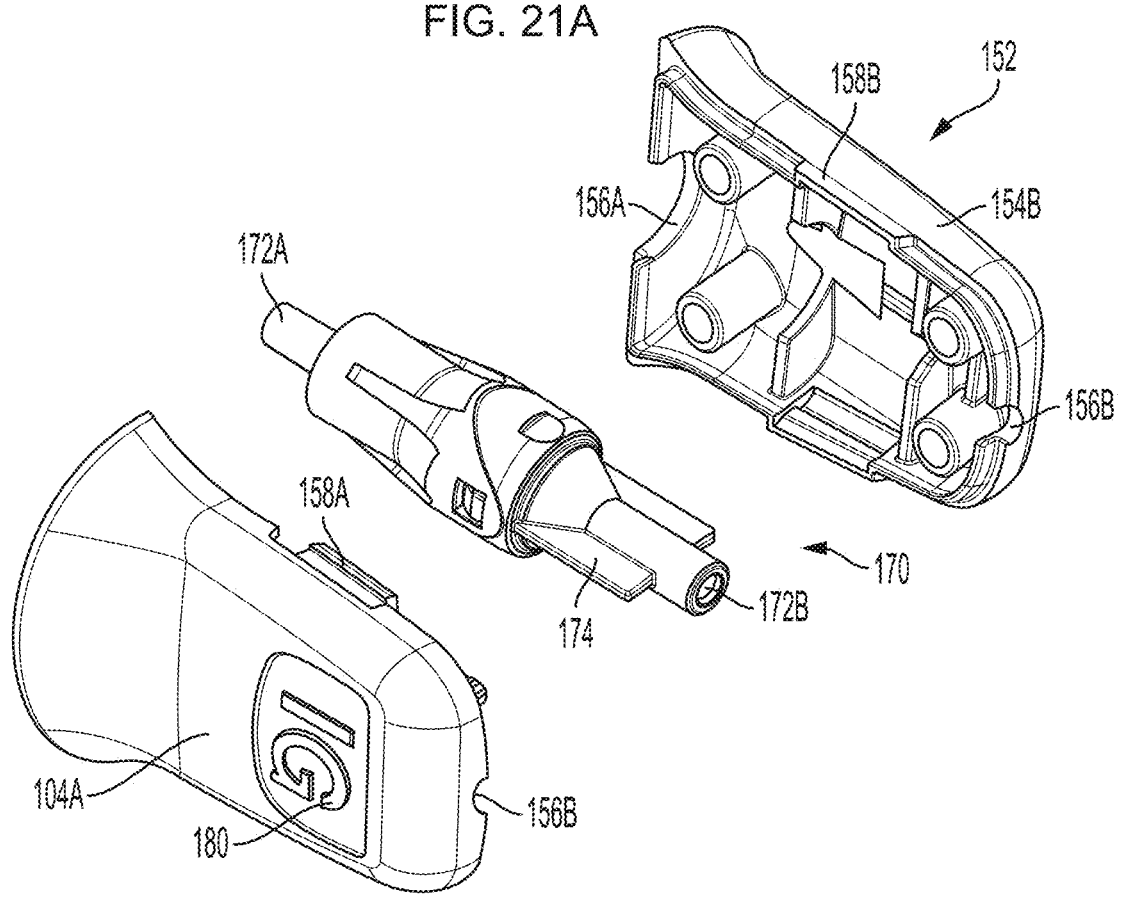
FIG. 21B is an exploded view of the fluidic interface of FIG. 21A.

FIG. 21B is an exploded view of the fluidic interface 152 of FIG. 21A. The housing of the fluidic interface includes a first portion 154A and a second portion 154B which may be coupled together by a latch 158A and a receptacle 158B. The housing defines an internal volume in which the male fluidic connector 170 may be at least partially disposed. The first aperture 156A and second aperture 156B provide access into the internal volume of the housing, either for components such as the male fluidic connector 170 and tubing 160, or for patient devices such as an infusion pump.

In the embodiment shown in FIG. 21B, the male fluidic connector 170 is configured to couple with an infusion pump so that fluid may be automatically withdrawn from the fluid distribution system by the infusion pump. The male fluidic connector may include a luer activated valve or any other suitable valve that may promote sterility or inhibit the flow of medicinal fluid prior to connection to the infusion pump. In some embodiments, the male fluidic connector may be configured to couple with other patient devices such as a syringe. The male fluidic connector includes a first end 172A and a second end 172B. In the embodiment shown in FIG. 21B, the first end 172A is disposed in and protrudes out from the first aperture 156A in the housing of the fluidic interface. The second end of the male fluidic connector is configured to couple with tubing to other components of a fluid distribution system. In the embodiment shown in FIG. 21B, the second end is disposed in the second aperture of the housing and is accessible from the second aperture to the tubing. The male fluidic connector also includes alignment features 174 which rotationally fix the male fluidic connector in the housing. In some embodiments, the alignment features 174 may be configured to fix the male fluidic connector translationally and rotationally relative to the housing of the fluid device. Accordingly, the housing and male fluidic connector may effectively function as a single component for the purposes of manipulation and handling by a patient or medical professional.

In some embodiments, the fluidic interface housing may have a flared, bell-shaped end. The bell-shaped end is configured to promote a gripping position by an operator (e.g., a patient or medical professional) which inhibits the operator from touching the fluidic connector of the fluidic interface. That is, the bell-shaped end promotes handling of the fluidic interface by the fluidic interface housing rather than the fluid connector during normal use, thereby maintaining cleanliness of the fluidic interface. Additionally, the bell-shaped end may be configured to be received by one or more latches on an associated housing of a pooling device. Such an arrangement may allow the fluidic interface to be releasably attached to the pooling device housing for convenient temporary or permanent storage before and/or after an administration process (for example, see FIG. 22B). The bell-shaped end may coincide with the first end of the fluidic connector. For example, as shown in FIG. 20A, housing 104 has a flared, bell-shaped end where the first end 122A of the fluidic connector 120 is located. As shown in FIG. 21A, housing 154 has a flared, bell-shaped end where the first end 172A of the fluidic connector 170 is located.

In some embodiments, the first end of a fluidic connector may be flush or recessed with the first aperture of a housing of a fluidic interface. Accordingly, the first aperture may provide access to the first end of the fluidic connector while additional protection is offered to the first end by the housing. Similarly, in some embodiments, the second end of a fluidic connector may be recessed or flush with a second aperture of the housing to offer additional physical protection for the second end while access is provided by the second aperture. In other embodiments, at least one of the first end and the second end of a fluidic connector may project out of the housing, so that easier access to the fluidic connector is provided. A fluidic interface may have any suitable arrangement of first and second ends of a fluidic connector including any combination of the aforementioned positions for each end of the fluidic connector relative to the housing, as the present disclosure is not so limited.

Figure 22A:
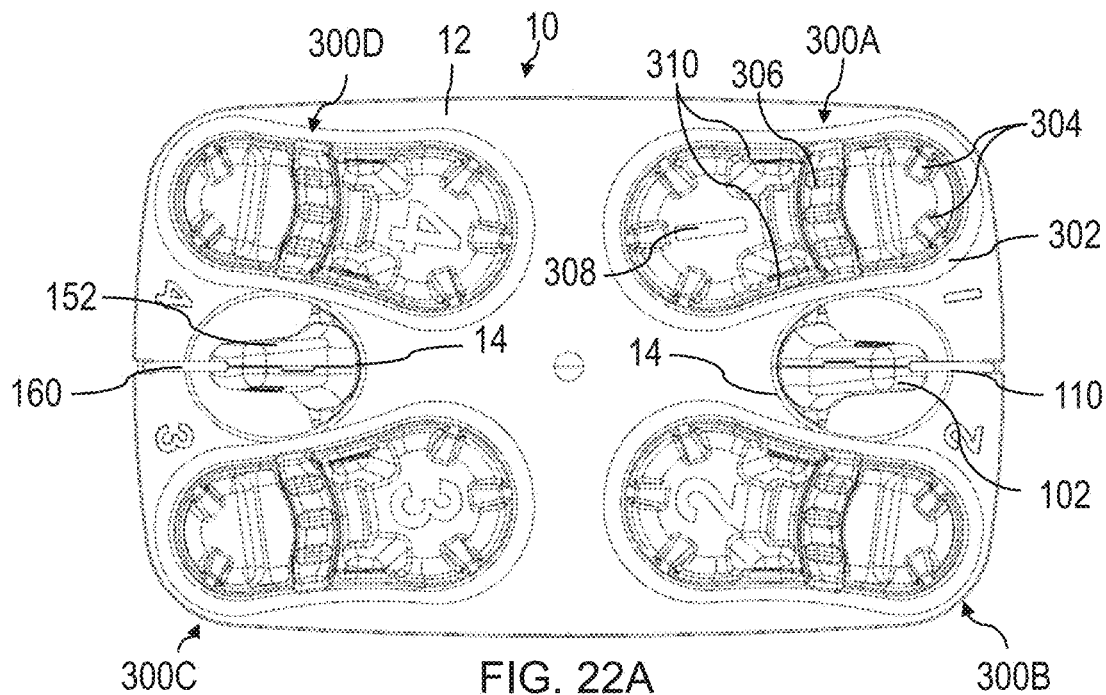
FIG. 22A is a top view of one embodiment of medicinal pooling device including covers.

FIG. 22A shows a top view of one embodiment of medicinal pooling device 10 including covers 300A, 300B, 300C, 300D. As discussed previously, the medicinal pooling device includes ports for receiving a container unit. Each of the ports is covered by a cover 300A, 300B, 300C, 300D which seals off the port and protects the spike assemblies disposed in the ports. Each cover may include a rim 302, ribs 304, a handle 306, a cover indicator 308 and latches 310. The rim is configured to seat the cover in a port and resist further movement into the port. Accordingly, the rim provides protection for the port and the spike assemblies disposed therein by supporting the cover over the port. The ribs are configured to provide structural rigidity for the cover, and ensure the cover is able to resist external forces and provide protection for the covered port. The handle 306 may include a textured surface that provides a solid surface by which a patient or medical professional can grab and remove the cover for use of the port. The handle or any other receiving portion may also receive any projections that extend out of the ports, such as alignment features. A receiving portion may have a shape complementary to that of a projection extending out of the ports, so that the projection may guide the associated cover when the cover is attached or removed. The cover indicator 308 may be used to convey information to a patient or medical professional regarding an administration process. For example, as shown in FIG. 22A, the cover indicators may indicate a desirable order in which to remove the covers and use the ports. The latches 310 of the cover may be used to removable secure the cover to the port. The latches may be breakable, bendable, or otherwise actuable so that a secured cover may be selectively removed by a patient or medical professional. In some embodiments, the latches 310 may be configured to release the cover when sufficient pulling force is applied to the handle 306.

Figure 22B:
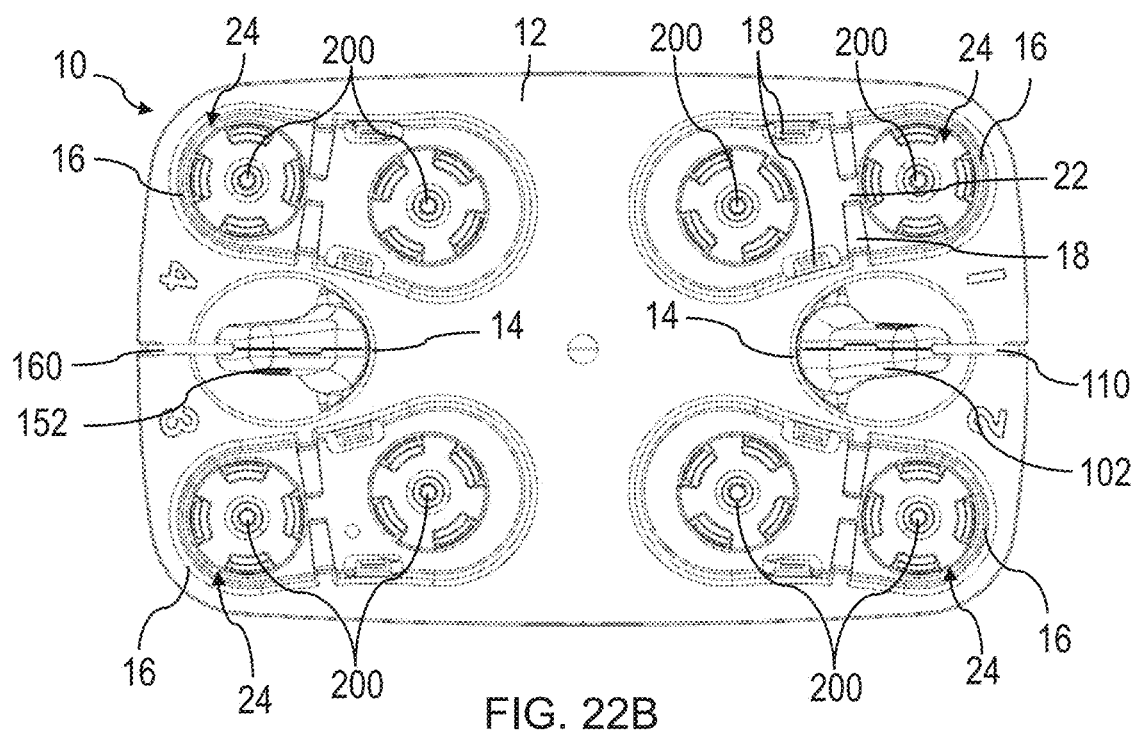
FIG. 22B is a top view of the medicinal pooling device of FIG. 22A with the covers removed.

FIG. 22B is a top view of the medicinal pooling device 10 of FIG. 22A with the covers 300A, 300B, 300C, 300D removed. As clearly shown in FIG. 22B, the ports 24 may be revealed for use when the covers are removed. Each port 24 may include at least one latch receptacle 18. The latch receptacles may receive the latches 310 disposed on the cover so that the cover may be removable secured to the port. The number of latch receptacles in the port may correspond to the number of latches disposed on the cover, so that a cover may be reliably secured to a port. According to the embodiment shown in FIGS. 22A-22B, the covers 300A, 300B, 300C, 300D have a shape corresponding to that of the ports 24. In some embodiments, the cover may be configured to press fit into a port to removably secure the cover to the port. That is, the cover may be tightly sized to fit in the port and is secured to the port by friction. Of course, the cover may include any suitable securing arrangement that may removably secure the cover to the port.

In some embodiments, the cover may be formed of a thermoformed plastic material. Accordingly, the cover may be thin and portions of a cover may be flexible where not reinforced by ribs 304. When significant force is applied to the cover to selectively remove the cover (e.g., pulling), the cover may flex to release the latches 310 or otherwise loosen the cover from the slot. In some embodiments, the rim 302 of the cover may include a pull tab (for example, see pull tab 312 in FIG. 24) that allows a patient or medical profession to remove the cover. According to this embodiment, if the cover is sufficiently flexible, a patient or medical profession may use the pull tab to peel the cover away from the port. Such an arrangement may reduce the force used to remove a cover to simplify operation. Of course, the cover may be formed of any suitable material, as the present disclosure is not so limited.

Figure 23:
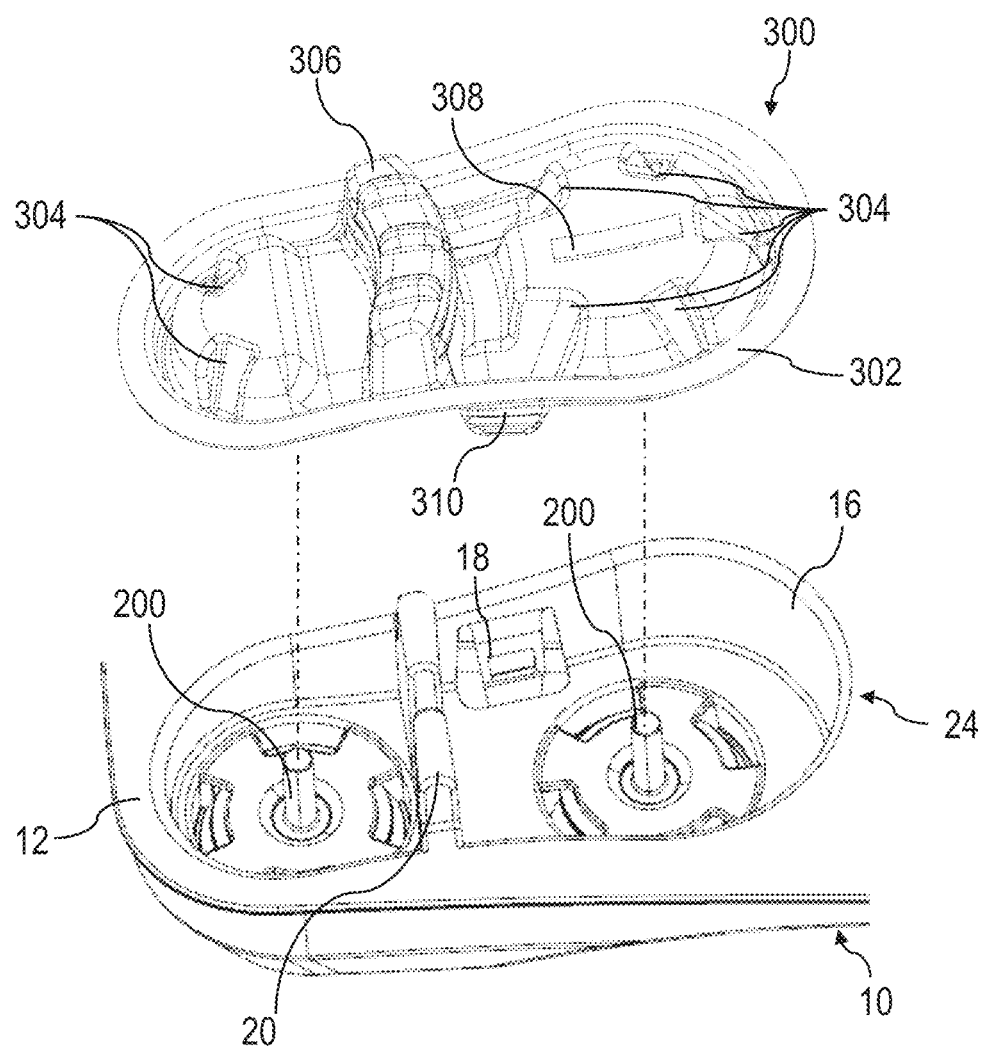
FIG. 23 is an exploded view of the medicinal pooling device and cover of FIG. 22A.

FIG. 23 is an exploded view of the medicinal pooling device 10 and cover 300 of FIG. 22A. As discussed previously, the cover includes a rim 302, ribs 304, a handle 306, a cover indicator 308, and a latch 310. The cover has a shape (e.g., perimeter shape) complementary to that of the port 24 formed in the housing 12 of the medicinal pooling device. The rim 302 is configured to abut the housing 12 when the cover is removable secured to the port. As shown in FIG. 23, the latches 310 are aligned with the latch receptacles 18 disposed on either side of the port. Accordingly, when the cover is in place over the port 24, the latch 310 engages that latch receptacle 18 to removably secure the cover to the port. In the embodiment of FIG. 23, the handle 306 may be pulled with sufficient force to bend the latches 310 to disengage the latch receptacles so that the cover may be selectively removed from the port. The handle 306 is also configured as a receiving portion which accommodates the guide projection 20 which extends out of the port 24.

As shown in FIG. 23, the ribs 304 of the cover are arranged radially around each of the spike assemblies 200. The ribs provide rigidity in the regions of the cover near the spike assemblies 200. That is, the covers are formed to provide the most protection and resistance to force above the spike assemblies in order to better protect the spikes during handling of the medicinal pooling device 10. As shown in FIG. 23, the regions of the cover surrounded by the ribs 304 may be raised to provide additional spacing between the cover and the spike assemblies. Accordingly, even if the covers are displaced towards the spike assemblies, the additional spacing may prevent contact between the spike and the cover. Of course, the ribs may be arranged in any suitable position on the cover where additional rigidity is desirable, as the present disclosure is not so limited.

Figure 24:
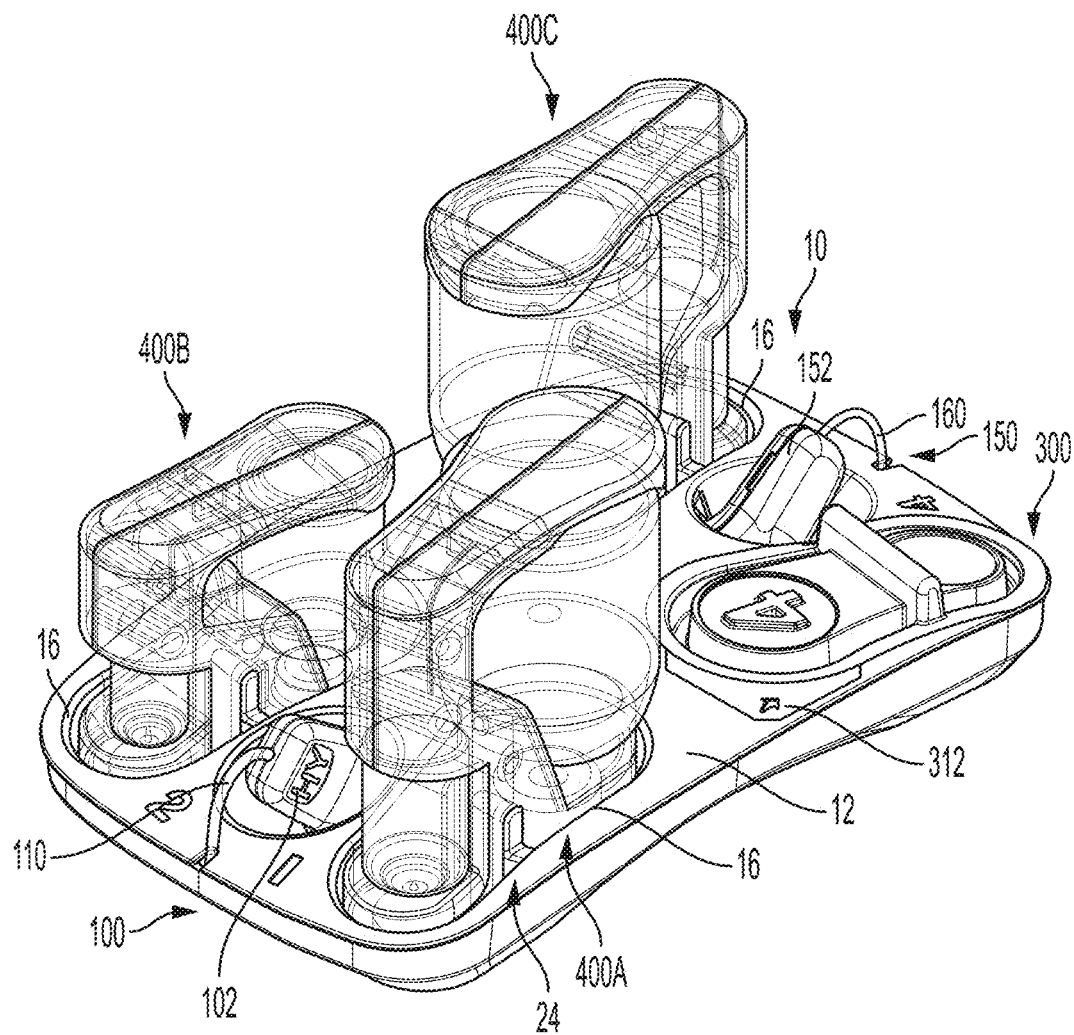
FIG. 24 depicts one embodiment of a medicinal pooling device in use with a plurality of container units.

FIG. 24 shows one embodiment of a medicinal pooling device 10 in use with a plurality of container units 400A, 400B, 400C. As shown in FIG. 24, the medicinal pooling device is pooling fluid from six separate containers, two containers in each container unit 400A, 400B, 400C connected to three of the four ports 24. Each of the container units has been inserted into a port in the medicinal pooling device after a cover associated with each port has been removed. As each container unit was inserted, the spikes pierced each of the two containers in the container unit to bring the containers into fluid communication with the two fluid distribution systems 100, 150 for pooling and delivery to the first fluidic interface 102 and the second fluidic interface 152.

As shown in FIG. 24, the number of ports used in the medicinal pooling device 10 may correspond to a particular dosage for administration to a patient. Accordingly, during an administration process, a patient or medical professional may remove only the covers from the ports to be used for the particular dosage desired. That is, covers may be left in place to maintain protection of a spike assembly if the port is not to be used for a particular dosage. In the embodiment shown in FIG. 24, the cover includes a pull tab 312 which may be used to peel up and remove a cover. Thus, during an administration process, a patient or medical professional may peel up a cover and subsequently connect a container unit to the port until the desired dosage of medicinal fluids is reached. After the container units are connected and the containers are fluidly connected to the fluid distribution system, the first and second fluidic interfaces 102, 152, may be connected to a patient device to supply medicinal fluids for injection or infusion into a patient.

Figure 25:
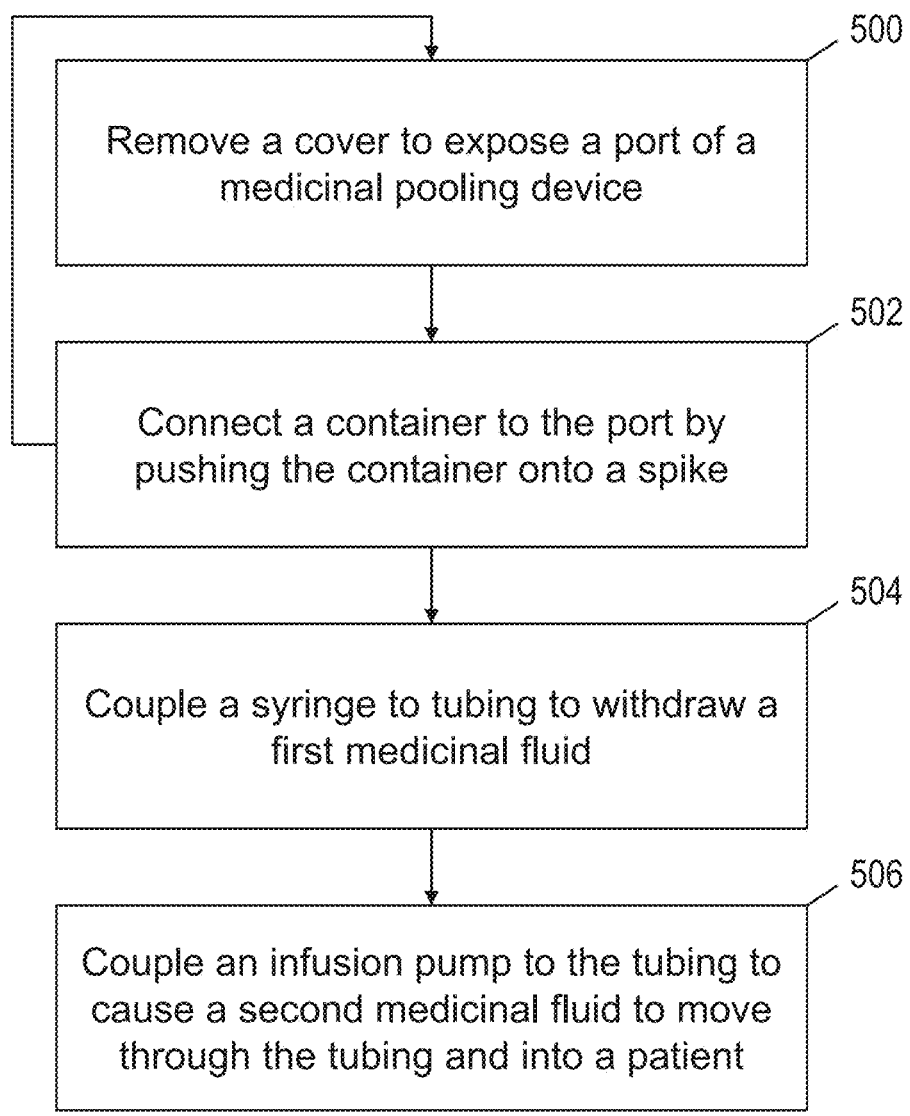
FIG. 25 is a block diagram of one embodiment of a method for operating a medicinal pooling device.

FIG. 25 is a block diagram of one embodiment of a method for operating a medicinal pooling device. In block 500, a patient or medical professional may remove a cover to expose a port of the medicinal pooling device. In block 502, the patient or medical profession may connect a container to the port by pushing the container onto a spike. As the container is push onto the spike, the container may be brought into fluidic communication with a fluid distribution system of the medicinal pooling device. Blocks 500 and 502 may be repeated as many times as necessary to reach a particular dosage of medicinal fluid. That is, for an increased dosage, additional covers may be removed and additional containers connected to additional ports. In block 504, a syringe may be coupled to tubing to withdraw a first medicinal fluid. The tubing may be a part of the medicinal pooling device brought into fluidic communication with the connected container(s), and may include a fluidic connector that may be used to connect the syringe to the tubing. In some embodiments, a patient or medical professional may inject the first medicinal fluid into the patient. In block 506, a patient or medical professional may couple an infusion pump to the tubing to cause a second medicinal fluid to move through the tubing and into the patient. The infusion pump may be coupled using the fluidic connector via a luer activated valve or any other suitable fluidic coupler. In some embodiments, the infusion pump may be used to withdraw the first medicinal fluid instead of a syringe.

In some embodiments, a medicinal pooling device may supply one or more medicinal fluids. Accordingly, depending on the number of fluids to be supplied by the pooling device, any number of patient devices may be coupled to the various fluid outlets of the pooling device. For example, infusion pumps, syringes, IV bags, and other suitable devices may all be coupled to the pooling device for eventual delivery of a medicinal fluid to a patient. In the embodiment of FIG. 25, one or more of blocks 504 and 506 may be eliminated from the method in cases where neither a syringe or infusion pump is appropriate to deliver the medicinal fluid from the pooling device. In some embodiments, one of block 504 and 506 and may be kept while the other is eliminated. For example, for delivery of a single fluid, a patient or medical professional may simply couple an infusion pump to the pooling device, without coupling a syringe at all. Any suitable combination of steps may be used to administer one or more medicinal fluids to a patient, as the present disclosure is not so limited.

Figure 26:
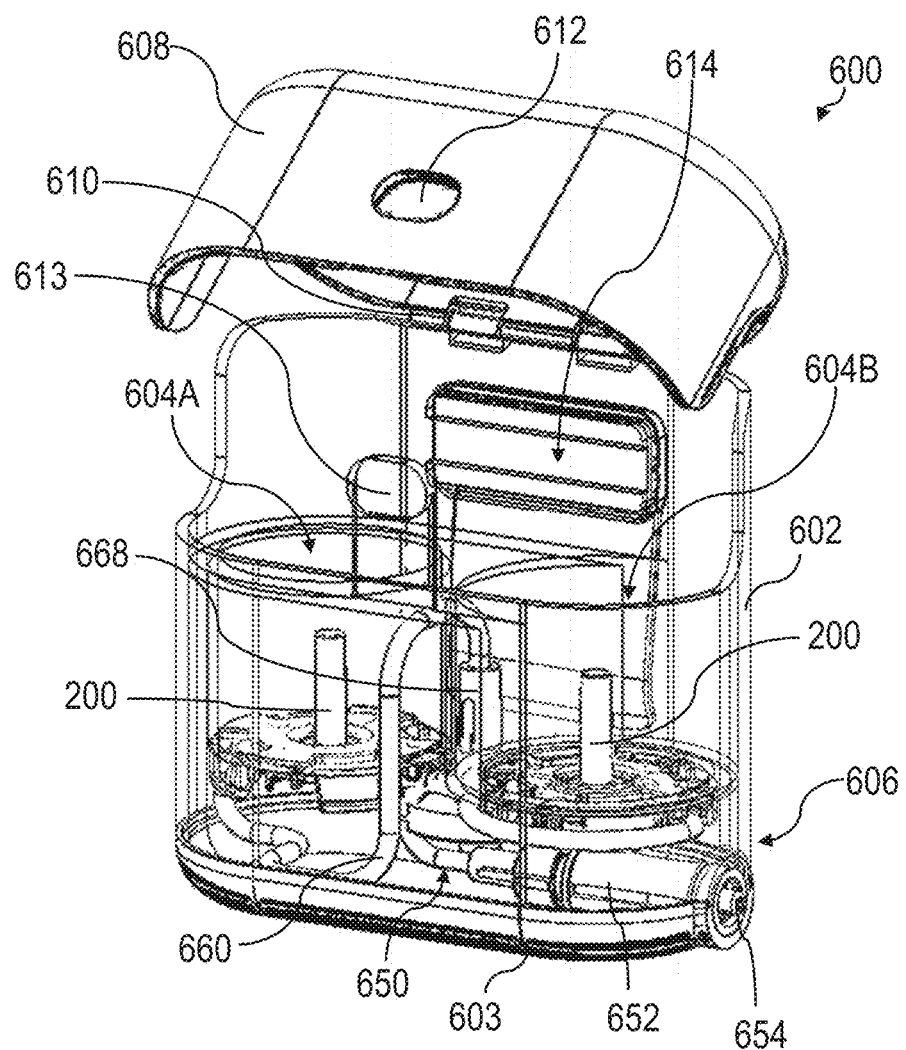
FIG. 26 is a perspective view of another embodiment of a medicinal pooling device.

FIG. 26 is a perspective view of another embodiment of a medicinal pooling device 600 which is configured to be worn by a patient to allow the patient free mobility during an administration process. Without wishing to be bound by theory, a worn device may affect mobility based at least partly on weight, weight distribution, and size. For example, a heavy, bulky object with a center of mass far away from a person may be cumbersome and may inhibit mobility when worn. Accordingly, the pooling device shown in FIG. 26 is configured to minimize the size of the pooling device to improve wearability while pooling medicinal fluids from multiple containers. As shown in FIG. 26, the pooling device 600 includes a housing 602 which is shown transparently for clarity. The pooling device also includes a first port 604A and a second port 604B which are formed side-by-side in the housing. As shown in FIG. 26, the first port and second port are formed close together and close to the extremities of the housing so that the overall size of the pooling device is minimized relative to the volume of containers being pooled. The pooling device also includes a base 603 which is configured to support the ports and other various components disposed in the housing.

According to the embodiment shown in FIG. 26, the pooling device may have a suitably small size for extended wearing by a patient without sacrificing pooling and fluid delivery functionality. In some embodiments, a total volume occupied by the pooling device may be less than or approximately equal to 800 $cm^3$, 700 $cm^3$, 600 $cm^3$, 500 $cm^3$, 400 $cm^3$, and/or any other appropriate volume. In some embodiments, the total volume of the pooling device may be between 500 and 700 $cm^3$. In some embodiments, a maximum longitudinal length of the pooling device may be less than or equal to 15 cm, 12 cm, 10 cm, 8 cm, and/or any other appropriate length. Correspondingly, in some embodiments, a maximum width of the pooling device may be less than or equal to 12 cm, 11 cm, 10 cm, 8 cm, and/or any other appropriate width. Similarly, in some embodiments, a maximum thickness of the pooling device may be less than or equal to 10 cm, 8 cm, 6 cm, 4 cm, and/or any other appropriate thickness. Such volumes and principal maximum dimensions may allow the pooling device to be easily worn with less interference with mobility. Of course, sizes greater than or less than those noted above may be employed, as the present disclosure is not so limited. Furthermore, a wearable pooling device may have any suitable dry weight, wet weight (i.e., with medicinal fluid containers attached), and weight distribution, as the present disclosure is not so limited.

According to the embodiment of FIG. 26, the pooling device includes a fluid distribution system 650 which is configured to pool fluid from containers which may be connected to the first port 604A and the second port 604B. As shown in FIG. 26, the pooling device includes spikes 200 disposed in the first port and second port, where the spikes are configured to pierce and fluidly connect a container of medicinal fluid to the pooling device. The spikes may include a spike sheath, shape, dual channels and/or other features according to exemplary embodiments described herein. The spikes are connected via tubing 660 which forms a continuous fluid channel terminating at one end in an air filter 668 and a fluidic outlet connector 652 on the other end. The air filter is configured to allow air into the fluid distribution system so that fluid contained in attached containers may flow freely under gravity or from pumping while preventing fluid from escaping. The fluidic outlet connector is secure in a fluid outlet port 606 formed in the housing 602 and is configured to receive a fluidic connector so that the fluid inside the fluid distribution system may be delivered to an associated device (e.g., infusion set, infusion pump, other drug delivery device, etc.), associated pooling device (e.g., for pooling fluid from multiple fluid pooling devices), or other desirable device or component. According to the embodiment of FIG. 26, the fluidic outlet connector 652 includes a luer activated valve 654 which prevents flow of fluid out from the fluid distribution system until an associated device or component having a corresponding luer activated valve is connected to the fluidic outlet connector. The luer activated valve 654 of FIG. 26 is a male luer activated valve configured to interface with a female luer activated valve. Of course, any suitable fluidic connector with or without a luer activated valve may be employed, as the present disclosure is not so limited.

According to the embodiment of FIG. 26, the pooling device may be configured to accommodate containers of medicinal fluid having a suitable volume for a prescribed dosage of the medicinal fluid. In some embodiments, each of the ports 604A, 604B may be configured to accommodate containers having a volumes greater than or approximately equal to 1.25 mL, 2.5 mL, 5 mL, 10 mL, 20 mL, 30 mL, 40 mL, 50 mL, and/or any other appropriate volume. Of course, a container with any suitable volume may be employed, as the present disclosure is not so limited.

According to the embodiment of FIG. 26, the pooling device may include a lid (e.g., cover) 608 which is configured to selectively enclose the first port 604A and the second port 604B to secure any containers disposed therein during an administration process. As shown in FIG. 26, the lid is attached to the housing 602 via a hinge 610. Accordingly, the lid is configured to rotate about the hinge between a closed position where the first port and the second port are completely enclosed and an open position where the first port and the second port are open so that they may receive containers of medicinal fluid. Of course, in other embodiments, the lid may be configured to interact with the housing in any suitable manner (e.g., being completely removable, sliding, etc.) to move between the open and closed positions, as the present disclosure is not so limited. As shown in FIG. 26, the lid includes a latch receptacle 612 which is configured to receive latch 613 disposed on the housing. The latch is configured as a deflectable latch which enters the latch receptacle to secure the lid when the lid is in the closed position and the latch is in an unbiased (i.e., unflexed) position. Conversely, the latch is configured to release the lid when the latch is moved to a biased position (i.e., flexed) position so that the latch is removed from the latch receptacle. Of course, any suitable latching arrangement may be employed, including, but not limited to, magnetic latches and spring-loaded catches.

As shown in FIG. 26, the pooling device may include a clip 614 configured to allow a patient to easily wear the pooling device. The clip is secured to the housing 602 and is configured to support the weight of the pooling device and any inserted containers. The clip is configured as a belt clip which may easily be slid over a belt to hold the infusion pump around the patient's hips. Of course, any suitable clip, strap, or harness may be employed to allow a patient to wear the pooling device, including, but not limited to, carabiners, hook and loop fasteners, strap buckles, a waist band, shoulder straps, etc., as the present disclosure is not so limited.

Figure 27:
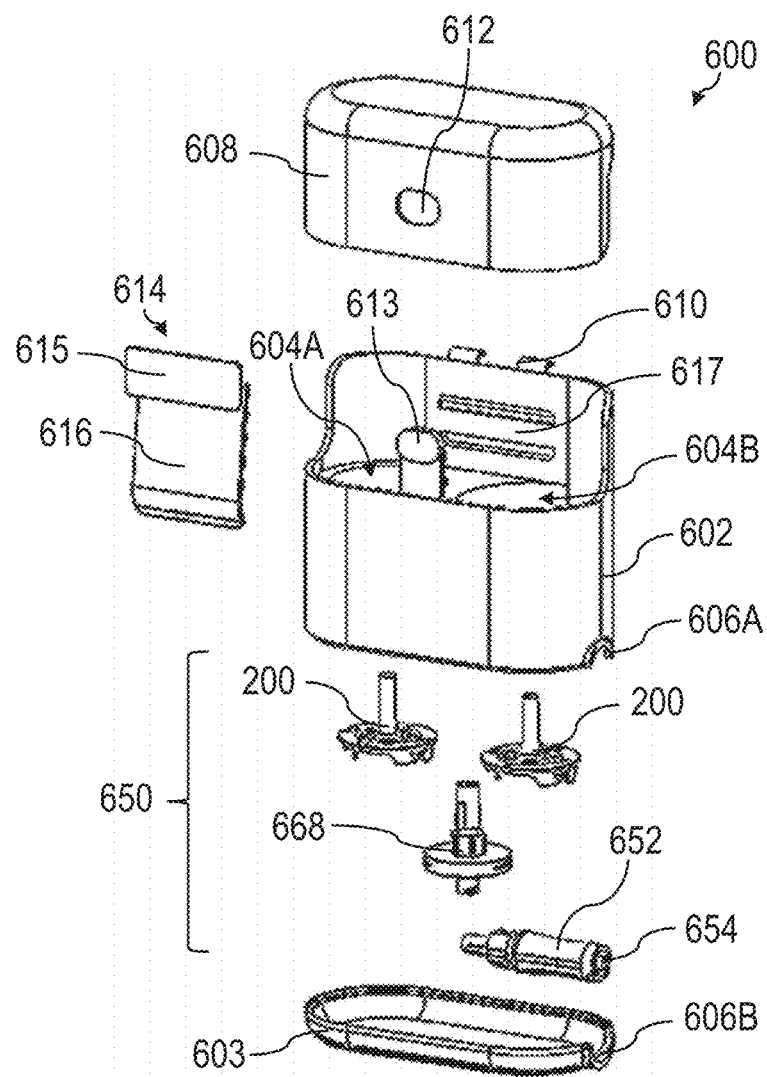
FIG. 27 is an exploded view of the medicinal pooling device of FIG. 26.

FIG. 27 is an exploded view of the medicinal pooling device 600 of FIG. 26. As noted previously, the pooling device includes a housing 602 having a first port 604A and a second port 604B, as well as a base 603. Disposed in the housing and supported by the base is the fluid distribution system 650, which includes spikes 200 disposed in each of the ports, an air filter 668, and a fluidic outlet connector 652 having a luer activated valve 654. The tubing of the fluid distribution system is omitted from FIG. 27 for clarity. The fluidic outlet connector 652 is configured to be secured between the housing and the base in outlet port portions 606A, 606B. The pooling device also includes a lid 608 which is mounted to the housing via hinge 610. The lid is selectively securable in a closed position with the latch 613 and the latch receptacle 612.

As shown in FIG. 27, the pooling device includes a clip 614 which allows the pooling device to be releasably coupled to clothing worn by a patient. The clip includes a mounting portion 615 and a flexible portion 616. The mounting portion 615 is configured to be secured to the clip receptacle 617 formed in the housing 602 of the pooling device. When the mounting portion 615 is received in or otherwise mounted to the clip receptacle 617, the mounting portion may support the entire weight of the pooling device when the clip is coupled to clothing worn by the patient. The flexible portion 616 is configured to be biased towards an exterior of the housing and to receive an article of clothing such as a belt. Accordingly, the flexible portion may be flexed away from the housing so that a belt or other article of clothing may be positioned between the flexible portion and the housing. When released, the flexible portion may releasably capture the belt or article of clothing between the flexible portion and the housing. Accordingly, the pooling device may be effectively suspended from the belt or article of clothing by the clip. To remove the article of clothing, the flexible portion may be flexed away from the housing once again and the belt or article of clothing may be removed. Of course, other arrangements of the clip are contemplated, including clips which are substantially rigid, and any suitable clip, clasp, latch, buckle, etc. may be employed to suspend the pooling device from clothing, as the present disclosure is not so limited.

Figure 28:
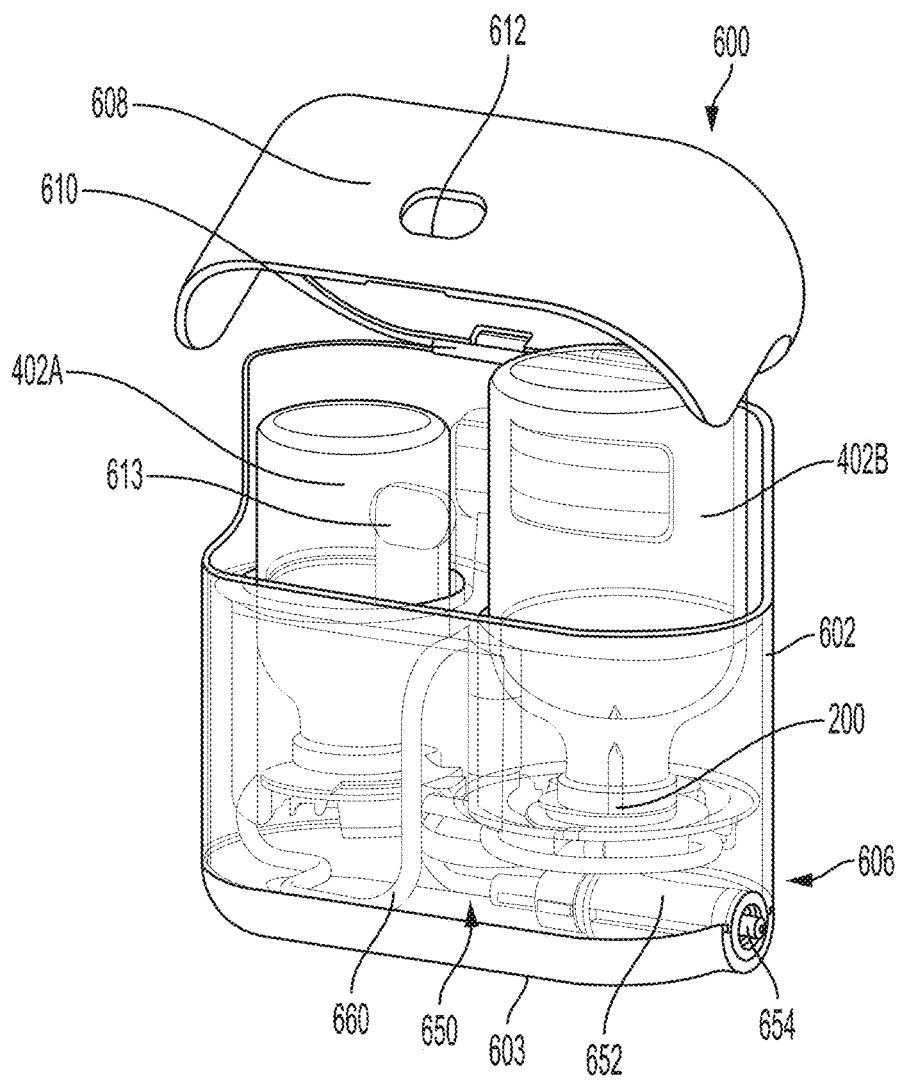
FIG. 28 is a perspective view of the medicinal pooling device of FIG. 26 in use with a plurality of containers.

FIG. 28 is a perspective view of the medicinal pooling device 600 of FIG. 26 in use with a first container 402A and a second container 402B. According to the embodiment shown in FIG. 28, the pooling device is pooling fluid from two differently sized containers. That is, the first container 402A has a smaller volume than the second container 402B. The pooling device supplies medicinal fluid from both containers at the fluidic outlet connector 652, so that a larger dosage than that supplied by either of the containers alone may be administered. As shown in FIG. 28, the spikes 200 are disposed in the internal volumes of the containers, so that the internal volumes of the containers are fluidly linked.

In contrast to previously described embodiments, the first port and second port are each configured to receive a single container of fluid as opposed to a container unit having more than one container. Accordingly, the first container and second container may be inserted into the first port and the second port, respectively, in a sequential manner. For example, a patient may insert the first container into the first port, thereby piercing the first container and bringing its internal volume into fluid communication with the fluid distribution system. Then, a patient may insert the second container into the second port, thereby piercing the second container and bringing its internal volume into fluid communication with the fluid distribution system. Once one or both containers are connected, fluid may be drawn from the fluidic outlet connector (e.g., through an infusion set, infusion pump, other drug delivery device, etc.).

As shown in FIG. 28, the pooling device lid 608 is in an open position and the containers 402A, 402B, and ports 604A, 604B, are exposed and accessible from outside of the housing 602. However, in the closed position, the lid is releasably secured with the latch 613 inside latch receptacle 612. Accordingly, when in the closed position, the lid will cover both of the containers and the ports, making them inaccessible from outside the housing. Such an arrangement may prevent unintentional removal of the containers from motion of the patient, bumps, or other forces.

Figure 29:
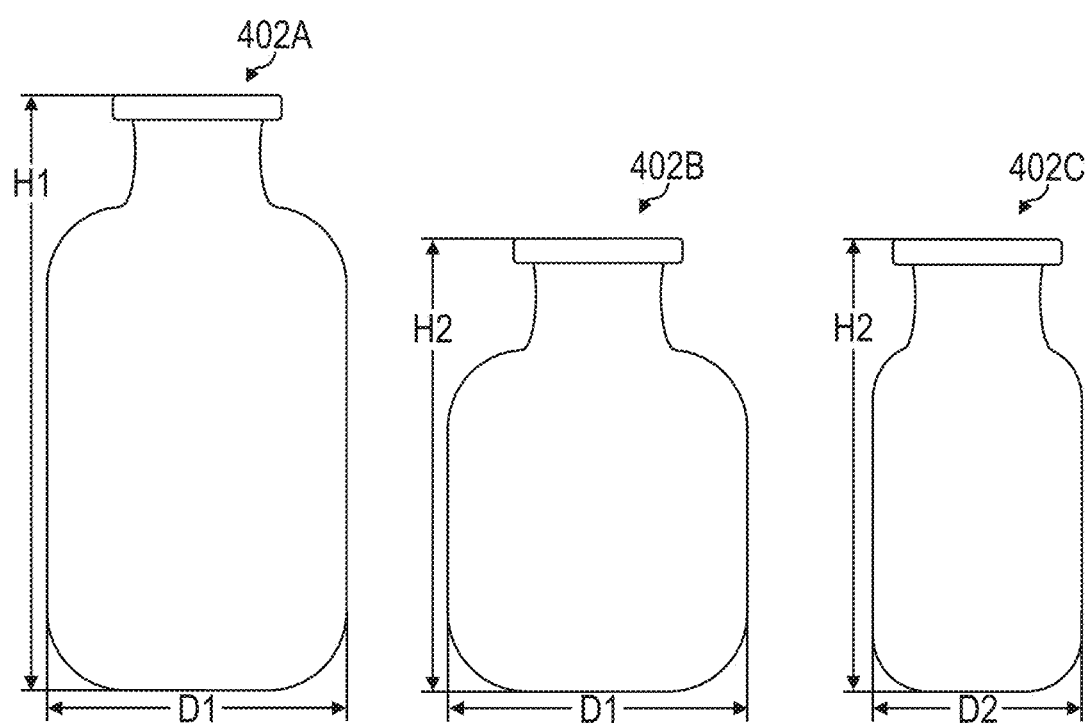
FIG. 29 is a front elevation view of various containers that may be used with the medicinal pooling device of FIG. 26.

FIG. 29 is a front elevation view of various containers that may be used with the medicinal pooling device of FIG. 26. Without wishing to be bound by theory, the pooling device according to the embodiment of FIG. 26 may be used with a wide variety of containers of medicinal fluid of different sizes. The containers may be sized and shaped according to the size and shape of the ports formed in the housing, or they may have any suitable shape that fits within the confines of the housing and the lid of the pooling device. As shown in FIG. 29, a first container 402A has a first height H1 and a first diameter D1, which may correspond to an internal height of a housing and diameter of a port of the pooling device. That is, the housing of the pooling device may accommodate containers having a height up to H1 and a diameter up to D1. In contrast, a second container 402B has a second height H2 but maintains the first diameter D1. Accordingly, the diameter of the second container corresponds to the internal diameter of a port on the pooling device, but the height does not correspond to an internal height of the housing. Nevertheless, containers with dimensions less than that of the internal dimensions of the housing may be accommodated in the pooling device, and may be held in place via features of the pooling device, e.g., friction with a spike, latches securing a collar of the bottle, or other suitable arrangements. As shown in FIG. 29, a third container 402C compatible with the pooling device includes a second height H2 and a second diameter D2 which are both less than that of the first container 402A. By accommodating different sizes of containers, the pooling device enables delivery of a precise dosage of medicinal fluid from a variety of standardized container sizes.

Figure 30A:
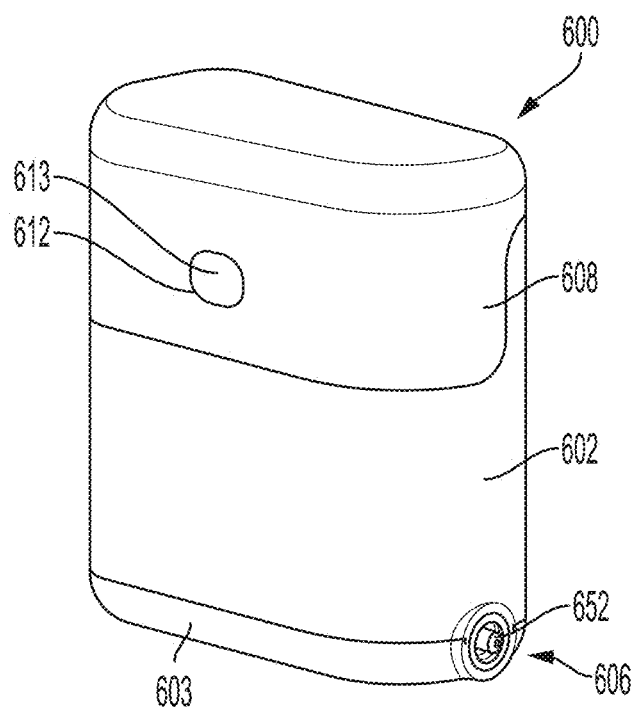
FIG. 30A is a front perspective view of the medicinal pooling device of FIG. 26 with a lid in a closed position.
Figure 30B:
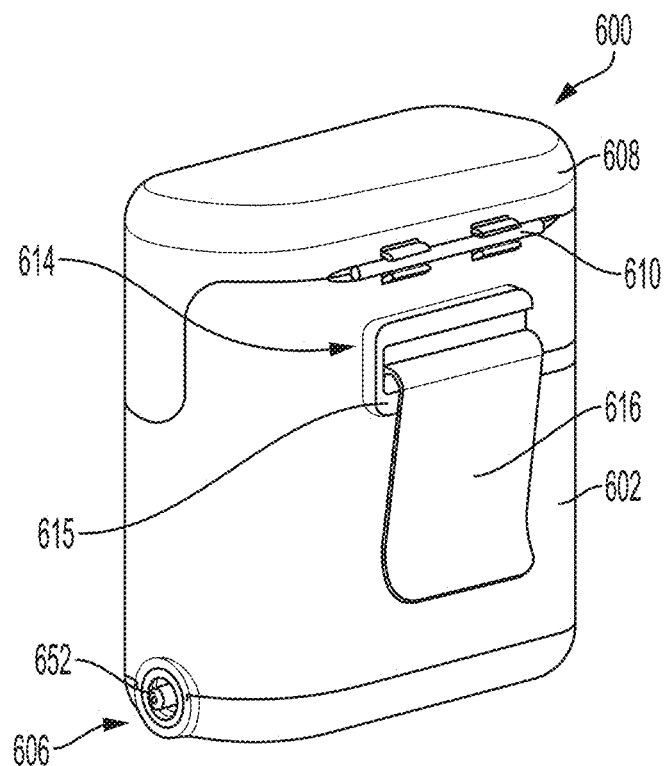
FIG. 30B is a rear perspective view of the medicinal pooling device of FIG. 26 with a lid in a closed position.

FIGS. 30A-30B depict a front perspective view and a rear perspective view, respectively, of the medicinal pooling device 600 of FIG. 26 with the lid 608 in a closed position. As best shown in FIGS. 30A-30B, when the lid is in the closed position, the latch 613 is disposed in the latch receptacle 612 to secure the lid in the closed position. Accordingly, the ports and any containers disposed therein are secured and protected from forces due to movement, bumps, etc., which may interfere with the fluid connection of the containers. Thus, the pooling device provides a compact, protected, and wearable package for pooling and delivering medicinal fluid from multiple containers.

Figure 31:
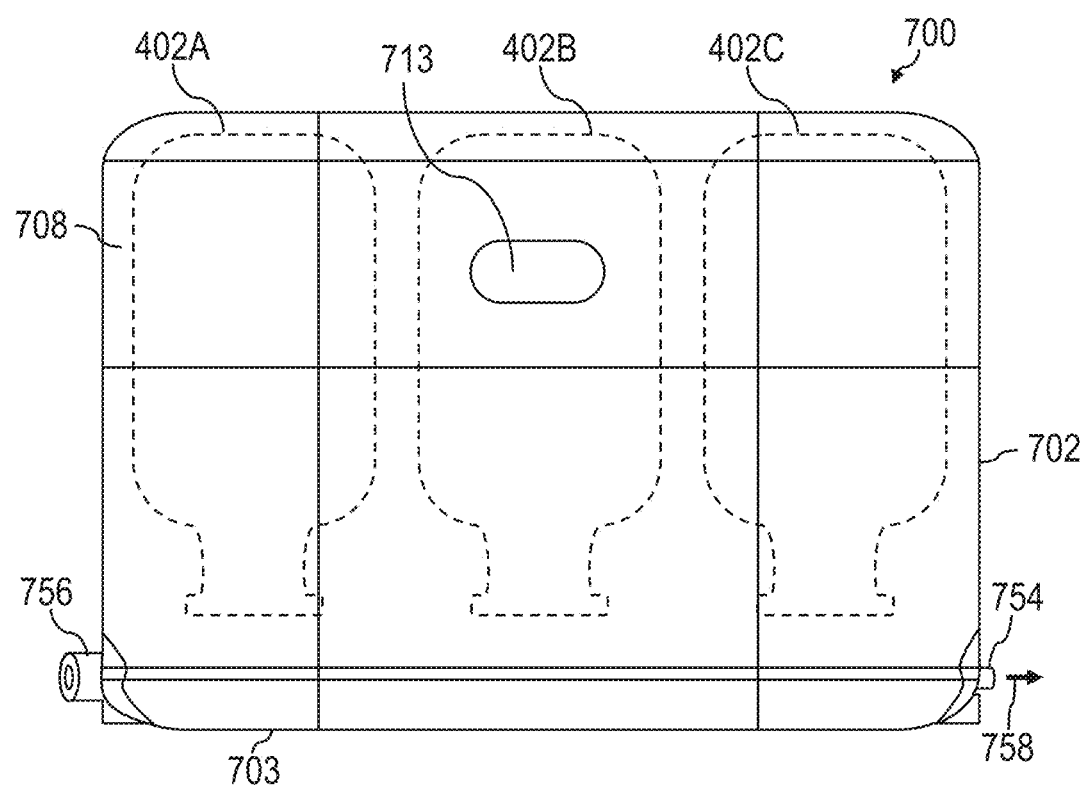
FIG. 31 is a front elevation view of another embodiment of a medicinal pooling device.

FIG. 31 is a front elevation view of another embodiment of a medicinal pooling device 700 configured to pool medicinal fluids from up to three containers. Similar to the embodiment of FIG. 26, the pooling device includes a housing 702, a base 703, and a lid 708. The lid is secured in a closed position by a latch 713, enclosing a first container 402A, a second container 402B, and a third container 402C disposed in ports formed in the housing. The pooling device includes a fluid distribution system (not shown) which creates a continuous fluidic channel between each of the containers. The fluid distribution system includes a fluidic outlet connector 754 and a fluidic inlet connector 756. According to the embodiment shown in FIG. 31, medicinal fluid is configured to flow from the containers to the fluidic outlet connector as indicated by arrow 758. Of course, in other embodiments, the medicinal fluid may flow in any suitable direction, including toward the fluidic inlet connector, as the present disclosure is not so limited. The outlet may be connected to an associated device (e.g., infusion set, infusion pump, other drug delivery device, etc.) or another pooling device to supply medicinal fluid from each of the three containers. The inlet is configured to receive medicinal fluid from another pooling device or associated medicinal fluid source, so that medicinal fluids may be pooled from multiple containers and/or multiple sources, if desired. The functionality of a fluidic inlet connector will be discussed further below with reference to FIGS. 32-35.

Figure 32:
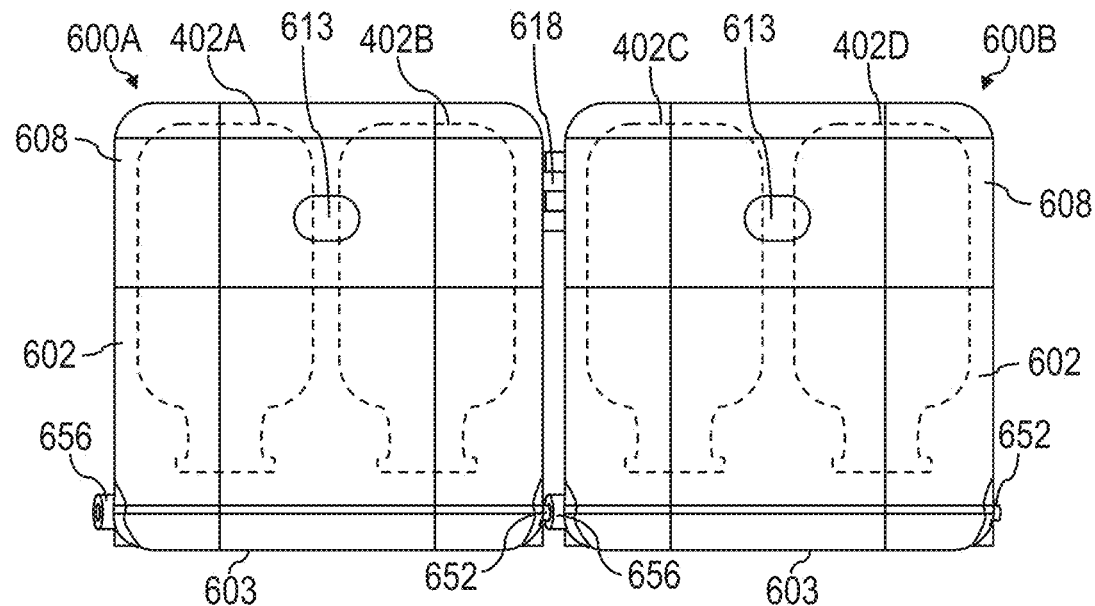
FIG. 32 is a front elevation view of one embodiment of a medicinal fluid pooling system.

FIG. 32 depicts a front elevation view of one embodiment of a medicinal fluid pooling system including a first wearable pooling device 600A and a second wearable pooling device 600B for pooling fluids from a larger number of containers than a single fluid pooling device. As shown in FIG. 32, each of the pooling devices is configured to accommodate two containers, with the first pooling device having a first container 402A and a second container 402B, while the second pooling device has a third container 402C and a fourth container 402D. Each pooling device includes a fluidic outlet connector 652 and a fluidic inlet connector 656 which allow the pooling devices to be connected in sequence. That is, as shown in FIG. 32, the fluidic outlet connectors are configured to connect to the fluidic inlet connectors of another pooling device. In particular, the fluidic outlet connector 652 of the first pooling device 600A is connected to the fluidic inlet connector 656 of the second pooling device 600B. The fluidic outlet connectors 652 of FIG. 32 include a male luer activated valve and the fluidic inlet connectors 656 include a female luer activated valve. Of course, in other embodiments, the fluidic outlet connector and inlet connector may employ any suitable mating or valve configuration, as the present disclosure is not so limited.

According to the embodiment of FIG. 32, the pooling devices include a physical connector 618 which is configured to physically secure the first wearable pooling device 600A to the second wearable pooling device 600B. In some cases, it is desirable to physically couple multiple wearable pooling devices together so that they may be handled as a single unit by a patient. However, it may also be desirable to permit flexibility of the combined pooling units so that the combined pooling device does not become cumbersome and affect wearability. Accordingly, as shown in FIG. 32, the physical connector 618 is configured as a hinge which allows the pooling devices to rotate relative to one another about a longitudinal axis (i.e., an axis running up and down relative to the page). Such an arrangement may allow the combined pooling units to conform to a shape of a patient's body when the combined pooling devices are worn. For example, the wearable pooling devices may wrap around a waist of the wearer so that both pooling devices may be easily suspended from a belt worn by a patient with a belt clip. Of course, the physical connector may be any suitable fastener which couples the motion of the pooling devices in at least one direction, as the present disclosure is not so limited.

Figure 33:
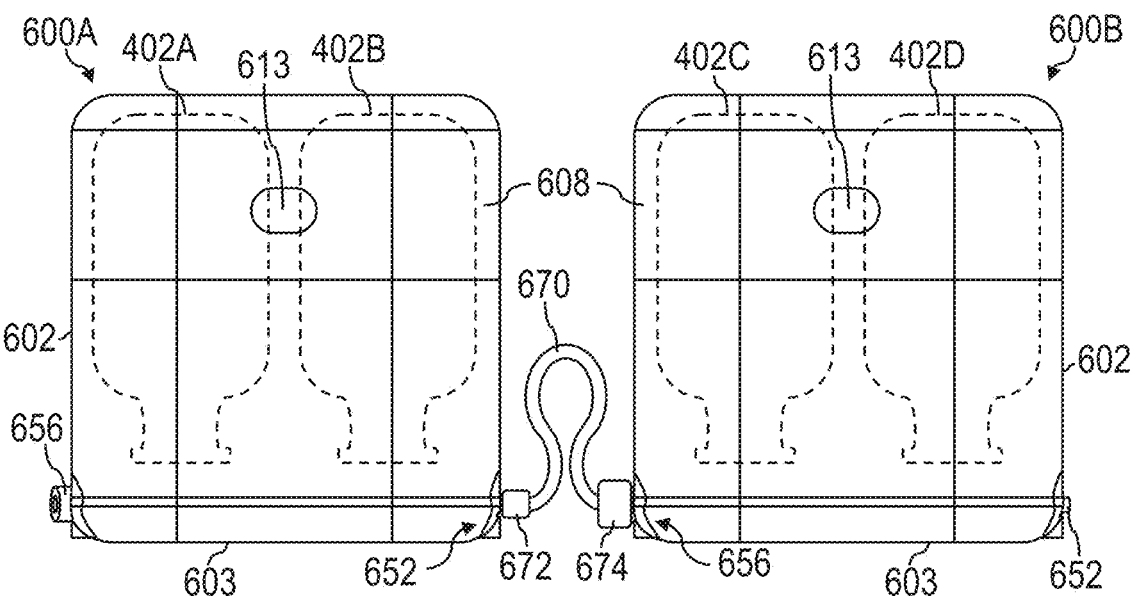
FIG. 33 is a front elevation view of another embodiment of a medicinal fluid pooling system.

FIG. 33 is a front elevation view of another embodiment of a medicinal fluid pooling system including a first wearable pooling device 600A and a second wearable pooling device 600B. In some cases, it may be desirable to allow connected pooling devices to be manipulated independently to allow the pooling devices to be independently secured to clothing or otherwise worn. Such an arrangement may improve the comfort of a wearer, as many small independent devices may be less cumbersome to wear or couple to clothing than a single large device. Accordingly, similar to the embodiment of FIG. 32, the fluidic outlet connector 652 of the first pooling device is connected to the fluidic inlet connector 656 of the second pooling device to allow administration of medicinal fluid from up to four containers 402A, 402B, 402C, 402D. However, in contrast to the embodiment of FIG. 32, the fluidic inlet connector and fluidic outlet connector are connected by pooling tubing 670 which allows free relative movement of the first pooling device and the second pooling device within a distance limit defined by the length of the tubing 670. Thus, the first wearable pooling device may be independently secured to the clothing or body of a patient to be worn before or after the pooling devices are connected with tubing. As shown in FIG. 33, the pooling tubing includes a tubing outlet connector 672 and a tubing inlet connector 674 which connect to a fluidic outlet connector 652 and a fluidic inlet connector 656 of the pooling devices, respectively. The pooling tubing may have any suitable length to allow a desirable range of independent movement and placement of the pooling devices.

According to the embodiments of FIGS. 32-33, a method for administering a medicinal fluid to a patient may include obtaining or providing a first wearable pooling device 600A and an optional second wearable pooling device 600B, and an associated number of containers for pooling a prescribed volume of medicinal fluid. The method may also include connecting a first container 402A to a first port formed in the first housing 602 of the first pooling device 600A, causing the first container to be pierced and brought into fluid communication with a fluid distribution system of the first pooling device. The method may further include connecting a second container 402B to a second port formed in the first housing of the first pooling device 600A, causing the second container to be pierced and brought into fluid communication with the fluid distribution system of the first fluid pooling device. If two containers are suitable for a prescribed dosage, the method may include connecting a fluidic outlet of the first pooling device to an infusion set, infusion pump, other drug delivery device, or other associated device for delivery to a patient. If additional containers are desired, the method may include connecting a third container 402C to the second wearable pooling device 600B in a manner similar to that of the first and second containers. Additionally, the method may include connecting a fourth container 402D to the second wearable pooling device, so that the second wearable pooling device pools fluid from both the third container and fourth container. Once a desirable number of containers is connected to the second wearable pooling device, the method may include connecting the second wearable pooling device to the first wearable pooling device (e.g., from a fluidic outlet connector of the second wearable pooling device to a fluidic inlet connector of the first wearable pooling device or vice versa). Alternatively, in some embodiments, the method may including delivering all of the medicinal fluid available from the first wearable pooling device to the patient, and subsequently disconnecting the first pooling device from the infusion set, infusion pump, other drug delivery device, or other associated device. In this embodiment, the method may further include connecting the second pooling device once the first pooling device is disconnected so that the delivery of fluid to the patient may be resumed. These methods may be repeated as necessary to pool and/or deliver a suitable volume of fluid to a patient. That is, any suitable number of pooling devices with connected containers may be sequentially coupled to one another or sequentially connected and disconnected from an infusion set, infusion pump, other drug delivery device, or associated device for delivering medicinal fluid to a patient, as the present disclosure is not so limited.

Figure 34:
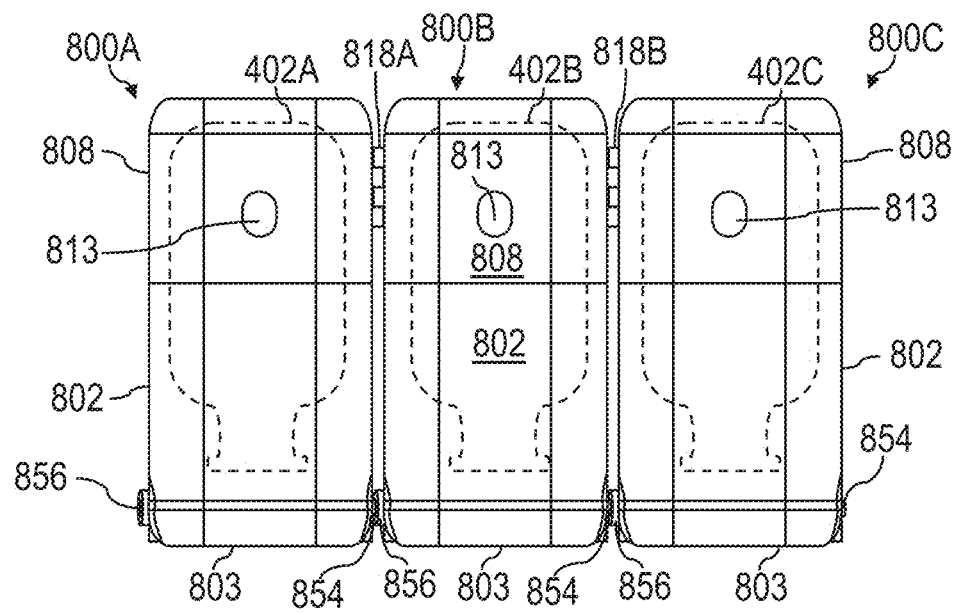
FIG. 34 is a front elevation view of yet another embodiment of a medicinal fluid pooling system.

FIG. 34 is a front elevation view of yet another embodiment of a medicinal fluid pooling system which includes a first wearable pooling device 800A, a second wearable pooling device 800B, and a third wearable pooling device 800C which provide a modular pooling system for fluidly connecting any desirable number of medicinal fluid containers. In particular, the medicinal fluid pooling system of FIG. 34 allows a patient to minimize the total volume and size of a pooling system to increase wearability while still being expandable to accommodate a variety of prescribed dosages. As shown in FIG. 34, each of the containers is configured to accommodate a single container. That is, the first pooling device includes a first container 402A, the second pooling device includes a second container 402B, and the third pooling device includes a third container 402C. The containers are secured inside ports formed in a housing 802 of each pooling device by a lid 808 which is held in a closed position with a latch 813. A base 803 of each pooling device supports the internal components of the pooling device. Similar to the embodiment of FIG. 32, the pooling devices include a first physical connector 818A and a second physical connector 818B which couple the pooling devices together to simplify handling and/or coupling to clothing or the patient's body.

Similar to the embodiments of FIGS. 32-33, each of the pooling devices 800A, 800B, 800C of FIG. 34 may be independently connected to one another, or to an infusion set, infusion pump, other drug delivery device, or other associated device. In the state shown in FIG. 34, a fluidic outlet connector 854 of the first pooling device is connected to a fluidic inlet connector 856 of the second pooling device 800B. A fluidic outlet connector 854 of the second pooling device is similarly connected to a fluidic inlet connector 856 of the third pooling device 800C. Accordingly, medicinal fluid from each of the containers disposed in the three pooling devices is pooled together and is accessible from a fluidic outlet connector 854 of the third pooling device 800C or, in some embodiments, the fluidic inlet connector 856 of the first pooling device 800A. Accordingly, fluid may be delivered to an infusion pump, infusion set, other drug delivery device, or other associated device from the three containers simultaneously. Of course, in other embodiments, any suitable number of pooling devices and containers may be employed to achieve a desired dosage of medicinal fluid, as the present disclosure is not so limited.

Figure 35:
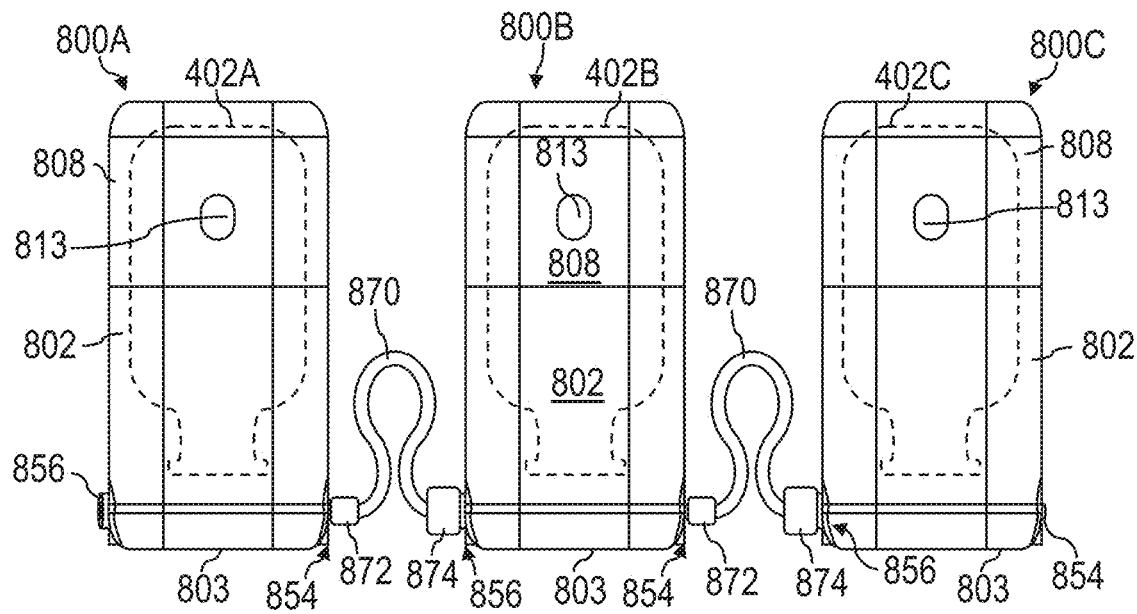
FIG. 35 is a front elevation view of still yet another embodiment of a medicinal fluid pooling system.

FIG. 35 is a front elevation view of still yet another embodiment of a medicinal fluid pooling system including a first wearable pooling device 800A, a second wearable pooling device 800B, and a third wearable pooling device 800C, which provide a modular pooling system for fluidly connecting any desirable number of medicinal fluid containers and for providing free movement of the pooling devices relative to one another within a distance limit defined by the length of the tubing 870. As noted previously, in some cases, it may be desirable to allow free relative movement of wearable pooling devices to simplify attaching the pooling devices to clothing or otherwise reduce the unitary bulk of a singular, connected pooling system. Accordingly, as shown in the embodiment of FIG. 35, the wearable pooling devices are interconnected with pooling tubing 870 which allows the pooling device to be independently movable relative to one another within a distance limit defined by the length of the tubing 870. The pooling devices of FIG. 35 are similar to those of FIG. 34, with each pooling device housing a single container (e.g., first container 402A, second container 402B, and third container 402C) and each pooling device including a fluidic inlet connector 856 and a fluidic outlet connector 854. Each of the pooling tubing 870 sets includes a tubing outlet connector 872 and a tubing inlet connector 874 which connect to a fluidic outlet connector 854 and a fluidic inlet connector 856 of the pooling devices, respectively. Accordingly, when the pooling tubing is connected, a continuous fluidic pathway is created between the internal volume of the containers disposed in each of the pooling device. In the embodiment of FIG. 35, an infusion set, infusion pump, other drug delivery device, or other associated device may be coupled to the fluidic outlet connector 854 of the third pooling device 800C to deliver fluid simultaneously from all three containers 402A, 402B, 402C. Of course, any suitable number of containers and pooling devices may be employed, as the present disclosure is not so limited. Additionally, rather than interconnecting the pooling device to one another, the pooling devices may be sequentially connected to the infusion set, infusion pump, other drug delivery device, or associated device to deliver an appropriate volume of fluid, as the present disclosure is not so limited.

Figure 36:
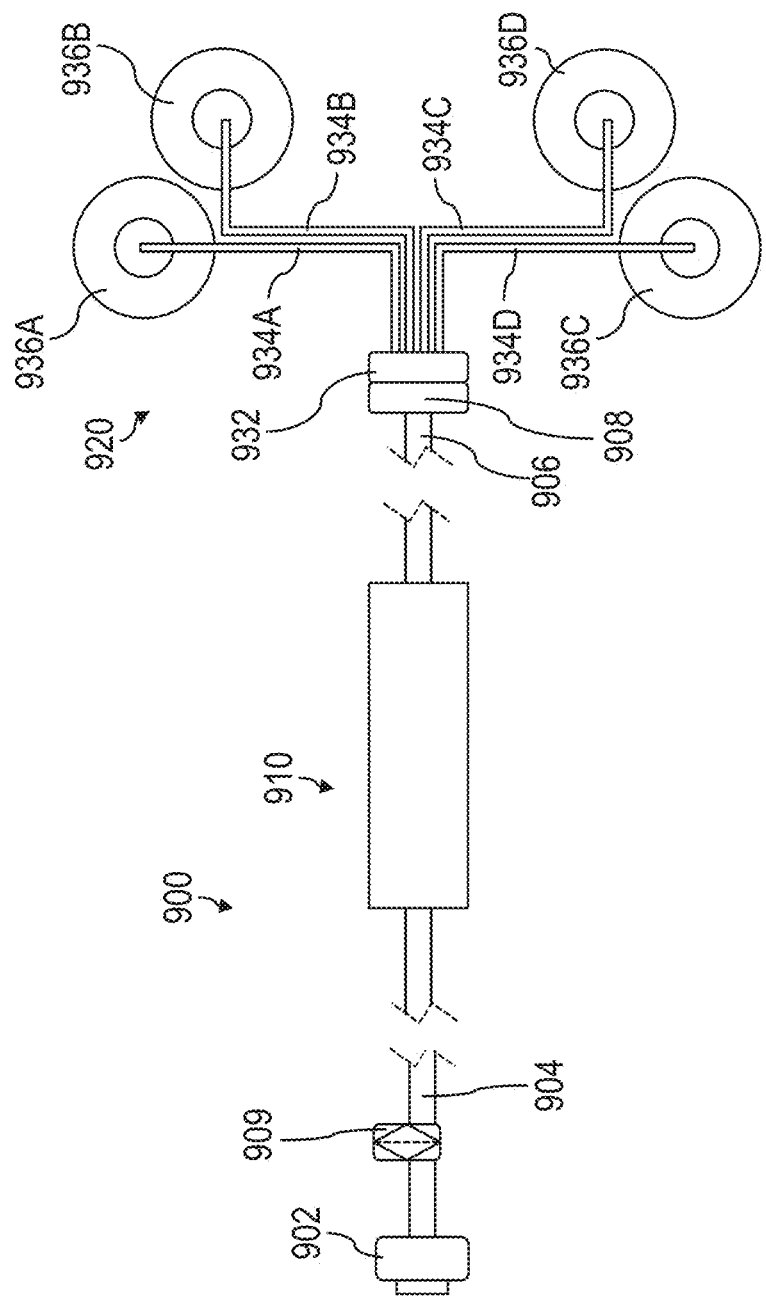
FIG. 36 depicts one embodiment of an infusion set for use with a medicinal pooling device.

FIG. 36 depicts one embodiment of an infusion set 900 having a breather valve (i.e., degassing valve, air release valve, etc.) 909 configured to allow the infusion set to be sequentially coupled and decoupled with one or more pooling devices according to exemplary embodiments described herein. As shown in FIG. 36, the infusion set includes an infusion set inlet 902, inlet tubing 904, a pump engine 910, outlet tubing 906, and an infusion set outlet 908 which together form a continuous fluid path. The pump engine is configured to pump fluid (e.g., from a pooling device) towards the infusion set outlet 908. The infusion set inlet 902 is configured to be coupled to a fluid supply such as a fluidic outlet connector, fluidic inlet connector, or other fluidic connectors of exemplary embodiments described herein. According to the embodiment of FIG. 36, the breather valve is positioned in-line with the inlet tubing 904. The breather valve is configured to vent air pockets that may be disposed in the inlet tubing. For example, when the infusion set is first used with a fluid supply, air inside the infusion set may be vented to prime the pump engine and/or allow fluid to flow from the fluid supply. Additionally, the breather valve may vent additional air bubbles that may form during fluid delivery to inhibit passage of air in the fluid stream. When the infusion set is disconnected from a first fluid supply (e.g., first pooling device), the infusion set may refill at least partially with air. Accordingly, when the infusion set is connected to a second fluid supply (e.g., second pooling device), the breather valve may once again vent air disposed in the infusion set to allow a continuous fluid stream to be delivered to a patient. Accordingly, the breather valve may permit swapping of fluid supplies without requiring a patient to switch infusion sets.

As shown in FIG. 36, the infusion set also includes a needle set 920 which is connected to the infusion set outlet 908 with a needle set connector 932. The needle set of FIG. 36 is quadfurcated, meaning the fluid channel from the infusion set outlet is split into a first needle channel 934A, a second needle channel 934B, a third needle channel 934C, and a fourth needle channel 934D. Disposed at the end of each needle channel is an infusion needle 936A, 936B, 936C, 936D which are usable to deliver fluid to a patient subcutaneously. Of course, in other embodiments, the needle set may include any suitable number of needles, including, but not limited to, a single needle, two needles (i.e., bifurcated), and three needles (i.e., trifurcated), as the present disclosure is not so limited.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A medicinal fluid pooling device, comprising:
   a spike sheath;
   a spike having a body including a first body portion, a second body portion, and a spike tip disposed on the first body portion, wherein the first body portion and second body portion have different cross sectional shapes, wherein the second body portion is configured to create a fluidic seal with the spike sheath, and wherein an internal channel of the spike extends through the first body portion and the second body portion;
   tubing in fluidic communication with the internal channel of the spike; and
   a base coupled to the spike, wherein the spike sheath is configured to compress and move towards the base when a force is applied to the spike sheath in a direction toward the base.

2. The medicinal fluid pooling device of claim 1, wherein the first body portion has a first major axis diameter and the second body portion has a second major axis diameter, wherein the first major axis diameter is larger than the second major axis diameter.

3. The medicinal fluid pooling device of claim 1, wherein the first body portion has a first minor axis diameter and the second body portion has a second major axis diameter, wherein the second major axis diameter is larger than the first minor axis diameter.

4. The medicinal fluid pooling device of claim 1, wherein the internal channel comprises an inlet and an outlet, wherein the inlet and the outlet are in fluidic communication via the spike sheath when the spike sheath is in an uncompressed position.

5. The medicinal fluid pooling device of claim 1, wherein the spike sheath includes a sheath base, a sheath shaft, and a sheath tip, wherein the spike is received in the sheath shaft, wherein the sheath shaft is configured to compress and move toward the sheath base when the force is applied to the spike sheath in the direction towards the base, wherein the spike pierces the sheath tip when the sheath shaft moves toward the base.

6. The medicinal fluid pooling device of claim 1, wherein the first body portion has an elliptical cross sectional shape and the second body portion has a circular cross sectional shape.

7. The medicinal fluid pooling device of claim 1, further comprising:
   a fluidic connector including a first end, a second end, and a luer activated valve controlling fluidic communication between the first end and the second end;
   a fluidic connector tubing in fluidic communication with the second end; and a housing including a first aperture and a second aperture, wherein the housing contains at least a portion of the fluidic connector, wherein the first end of the fluidic connector is accessible.

8. The medicinal fluid pooling device of claim 7, wherein the housing includes a bell-shaped end proximate the first aperture.

9. The medicinal fluid pooling device of claim 8, wherein the bell-shaped end is configured to be received by one or more latches disposed on the medicinal fluid pooling device.

10. The medicinal fluid pooling device of claim 1, further comprising:
a port including the spike; and
a cover configured to removably connect to the port to cover the spike.

11. The medicinal fluid pooling device of claim 10, wherein the cover includes a pull tab configured to be pulled by an operator to disconnect the cover from the port.

12. The medicinal fluid pooling device of claim 10, wherein a perimeter of the port and a perimeter of the cover have complementary shapes, wherein the cover is at least partially inserted into the port when the cover is removably connected to the port.

13. The medicinal fluid pooling device of claim 10, wherein the cover includes a receiving portion configured to receive a projection disposed in the port.

\* \* \* \* \*

UNITED STATES PATENT AND TRADEMARK OFFICE
CERTIFICATE OF CORRECTION

Page 1 of 1

PATENT NO. : 12,214,161 B2
APPLICATION NO. : 17/282042
DATED : February 4, 2025
INVENTOR(S) : Seth Dale Jones et al.

It is certified that error appears in the above-identified patent and that said Letters Patent is hereby corrected as shown below:

On the Title Page

After the Section "Prior Publication Data" please add --Related U.S. Application Data Provisional application No. 62/819,349, filed on Mar. 15, 2019, provisional application No. 62/740,475, filed on Oct. 3, 2018--

Signed and Sealed this
Twenty-fifth Day of March, 2025

Coke Morgan Stewart
*Acting Director of the United States Patent and Trademark Office*